US007166584B1

(12) United States Patent
Attie et al.

(10) Patent No.: US 7,166,584 B1
(45) Date of Patent: Jan. 23, 2007

(54) CHOLESTEROL TRANSPORT GENE

(75) Inventors: Alan D. Attie, Madison, WI (US); Mark Cook, Madison, WI (US); Mark P. Gray-Keller, Middleton, WI (US); Michael R. Hayden, Vancouver (CA); Simon Pimstone, Vancouver (CA); Angela R. Brooks-Wilson, Vancouver (CA)

(73) Assignees: Wisconsin Alumni Research Foundation, Madison, WI (US); Xenon Genetics, Inc., Burnaby (CA)

( * ) Notice: Subject to any disclaimer, the term of this patent is extended or adjusted under 35 U.S.C. 154(b) by 0 days.

(21) Appl. No.: 09/704,272

(22) Filed: Nov. 1, 2000

Related U.S. Application Data

(60) Provisional application No. 60/215,564, filed on Jun. 30, 2000, provisional application No. 60/162,803, filed on Nov. 1, 1999.

(51) Int. Cl.
*A01N 57/00* (2006.01)
*A61K 49/00* (2006.01)
(52) U.S. Cl. .................................. 514/107; 424/9.1
(58) Field of Classification Search ............. 424/130.1, 424/9.1; 530/350; 536/23.5; 435/35; 514/107
See application file for complete search history.

(56) References Cited

U.S. PATENT DOCUMENTS

| 5,725,873 A | 3/1998 | Cook et al. |
| 5,814,316 A | 9/1998 | Cook et al. |

FOREIGN PATENT DOCUMENTS

| WO | WO98/57649 | 12/1998 |
| WO | WO00/18912 | 4/2000 |
| WO | WO00/34461 | 6/2000 |
| WO | WO00/55318 | 9/2000 |

OTHER PUBLICATIONS

Lawn, et al, 1999, J. Clinical Investigation, 104: R25.*
Berge, et al, 2000, Science, 290: 1771.*
Remaley, et al, 1999, Proc. Natl. Acad. Sci., 96(22): 12685-12690.*
Asztalos, et al, 2001, Atherosclerosis, 156: 217-225.*
Goodman and Gilman, The Pharmacological Basis of Therapeutics, 1993, McGraw-Hill, pp. 1484-1488.*
Pettit and Gombotz, 1998, TIBTECH, 16: 343-349.*
Becq, F. et al., "ABC1, an ATP Binding Cassette Transporter Required for Phagocytosis of Apoptotic Cells, Generates a Regulated Anion Flux after Expression in *Xenopus laevis* Oocytes," *The Journal of Biological Chemistry* 272:2695-2699 (1997).
Bodzioch, M. et al., "The gene encoding ATP-binding cassette transporter 1 is mutated in Tangier disease," *Nature Genetics* 22:347-351 (1999).
Brooks, A. et al., "Mutations in ABC1 in Tangier disease and familial high-density lipoprotein deficiency," *Nature Genetics* 22:336-345 (1999).

Fridolfsson, A.K. et al., "Evolution of the avian sex chromosomes from an ancestral pair of autosomes," *Proc. Natl. Acad. Sci. USA* 95:8147-8152 (1998).
McNeish, J. et al., "High density lipoprotein deficiency and foam cell accumulation in mice with targeted disruption of ATP-binding cassette transporter-1," *PNAS* 97:4245-4250 (2000).
Orso, E. et al., "Transport of lipids from Golgi to plasma membrane is defective in Tangier disease patients and Abc1-deficient mice," *Nature Genetics* 24:192-196 (2000).
Poernama, F. et al., "Spontaneous high density lipoprotein deficiency syndrome associated with a Z-linked mutation in chickens," *Journal of Lipid Research* 31:955-963 (1990).
Poernama, F. et al., "High Density Lipoprotein Deficiency Syndrome in Chickens Is Not Assciated With an Increased Susceptibility to Atherosclerosis," *Arteriosclerosis and Thrombosis* 12:601-607 (1992).
Repa, J.J. et al., "Regulation and Absorption and ABC1-mediated Efflux of Cholesterol by RXR Heterodimers," *Science* 289:1524-1529 (2000).
Rust, S. et al., "Tangier disease is caused by mutations in the gene encoding ATP-binding cassette transporter 1," *Nature Genetics* 22:352-355 (1999).
Schreyer, S.A. et al., "Hypercatabolism of Lipoprotein-Free Apolipoprotein A-I in HDL-Deficient Mutant Chickens," *Arteriosclerosis and Thrombosis* 14:2053-2059 (1994).
Yokoyama, H. et al., "Detection of passage and absorption of chicken egg yolk immunoglobulins in the gastrointestinal tract of pigs by use of enzyme-linked immunosorbent assay and fluorescent antibody testing," *Am J Vet Res* 54:867-872 (1993).
Young, S.G. et al., "The ABCs of cholesterol efflux," *Nature Genetics* 22:316-318 (1999).
Hamon et al., Interleukin-1β Secretion is Impaired by Inhibitors of the Atp Binding Cassette Transporter, ABC1, *Blood* 90:2911-2915 (1997).
Owen, James S., "Role of ABC1 gene in Cholesterol efflux and atheroprotection," *The Lancet* 354:1402-1403 (1999).
Schmita, et al., ATP-Binding Cassette Transporter A1(ABCA1) in Macrophages: A Dual Function in Inflammation and Lipid Metabolism? *Pathobiology* 67:236-240 (1999).

* cited by examiner

*Primary Examiner*—Brenda Brumback
*Assistant Examiner*—Sandra Wegert
(74) *Attorney, Agent, or Firm*—Quarles & Brady LLP

(57) ABSTRACT

Methods and compounds are disclosed for lowering serum LDL levels or serum cholesterol levels, or for reducing the transport of cholesterol from the gut to the blood or the lymph, based on the observation that a gene known as ABC1 is necessary in order for cholesterol to be transported from the intestinal lumen into the bloodstream. A mutant chicken phenotype, known as the WHAM chicken, characterized by low levels of serum LDL and reduced transport of cholesterol, facilitated the discovery of this function of the ABC1 gene. Techniques which act to inhibit ABC1 activity in the cells of the intestinal wall will result in lower serum cholesterol.

4 Claims, 4 Drawing Sheets

CHOLESTEROL TRANSPORT GENE

CROSS REFERENCE TO RELATED APPLICATION

This application claims the benefit of U.S. Provisional patent applications Ser. No. 60/162,803 filed Nov. 1, 1999 and Ser. No. 60/215,564 filed Jun. 30, 2000.

BACKGROUND OF THE INVENTION

Cholesterol is one of the most intensely studied of molecules that circulate in the human bloodstream. Cholesterol is a lipid that is a major component of cell membranes and also is the precursor of steroid hormones and the bile acids. Two sources of cholesterol are available to cells. Endogenous cholesterol is synthesized in the liver and other cells and transported through the bloodstream to other cells. Since cholesterol is highly apolar, it is transported through the bloodstream in the form of lipoproteins consisting essentially of a core of apolar molecules such as cholesterol surrounded by an envelope of polar lipids, primarily phospholipids. Alternatively, exogenous cholesterol may be absorbed from the gut. Exogenous cholesterol is transported from the lumen of the gut into the blood or lymph for distribution via lipoprotein particles to other cells of the body.

For the diagnostic purposes related to human health, the lipoproteins are classified into several categories based on the density of the lipoprotein particles. The two categories most discussed in connection with human health are the low-density lipoproteins (LDL) and the high-density lipoproteins (HDL). For many people, HDL is known as the "good cholesterol" since it has a somewhat protective effect on the tendency of LDL to contribute toward coronary artery disease and related cardiovascular conditions such as stroke. Studies have shown an inverse relationship between levels of serum HDL and the occurrence of coronary artery disease, resulting in HDL levels being graded as a strong risk factor for cardiovascular disease prediction. Accordingly, a low level of HDL cholesterol, referred to as hypoalphalipoproteinemia, is a blood abnormality that correlates with increased risk of cardiovascular disease.

One rare form of genetic HDL deficiency is known as Tangier disease. Patients with the homozygous form of this disease have an almost total absence of serum HDL cholesterol. The disease is an autosomal recessive trait, and patients with the disease accumulate cholesterol esters in several tissues, resulting in characteristic physical features including enlarged orange or yellow tonsils, hepatosplenomegaly, peripheral neuropathy, and cholesterol deposition in the rectal mucosa. The symptoms of the disease appear to be attributable to a deficiency in cholesterol and/or phospholipid transport across cell membranes, principally out of cells that manufacture or store excess cholesterol. The orange tonsils are, for example, caused by the accumulation of cholesterol esters and related carotenoids in macrophages. It has now been established that Tangier Disease is a monogenic disorder caused by a mutation in the ABC1 gene (Brooks-Wilson, A. et al. 1999, "Mutations in ABC1 in Tangier disease and familial high-density lipoprotein deficiency." *Nat. Genet.* 22:336–345; Bodzioch, M. et al. 1999, "The gene encoding ATP-binding cassette transporter 1 is mutated in Tangier Disease." *Nat. Genet.* 22:347–351; Rust, S., et al. 1999, "Tangier Disease is caused by mutations in the gene encoding ATP-binding cassette transporter 1." *Nat. Genet.* 22:352–355). Other patients exhibit a more common form of genetic HDL deficiency which results in low plasma HDL and premature cardiovascular disease, but an absence of the severe symptoms associated with Tangier disease. A large sub-group of patients with low HDL have an inherited form of this disease, familial hypoalphalipoproteinemia (FHA). It has been found that many of these patients are heterozygotes for mutations in ABC1. (Brooks-Wilson, A. et al. 1999, supra). Thus, ABC1 in its homozygous form causes Tangier disease and in its heterozygous form causes FHA.

An animal model for low HDL conditions exists in the form of the Wisconsin Hypo-Alpha Mutant (WHAM) chicken. This single gene mutation arose naturally and was identified because of the white skin phenotype and a closed flock of the chickens has been maintained as an animal model for low HDL disease. (Poernama et al. *Jour. Lipid Res.* 31:955–963 (1990)). The effect of this mutation on diet-induced atherosclerosis has been investigated, and it has been found that WHAM chickens are highly deficient in their ability to transport cholesterol from the gut into the blood. (Poernama et al. *Arteriosclerosis and Thrombosis* 12:2:601–607 (1992)). Some efforts have been made to identify the genetic element responsible for the mutation in the WHAM chickens (Schreyer et al. *Arteriosclerosis and Thrombosis* 14:12:2053–2059 (1994)), but prior to the instant invention, these efforts have not been successful.

It is highly desirable to identify and develop compounds and therapeutic agents which are useful for reducing cholesterol transport from the gut to the blood or lymph and for the regulation and treatment of cardiovascular disorders (such as high LDL or serum cholesterol levels), obesity, elevated body-weight index and other disorders relating to lipid metabolism.

SUMMARY OF THE INVENTION

The present invention is summarized in that a method is described for the lowering of levels of LDL cholesterol in an individual comprising administering to the individual an agent which modulates the activity of the ABC1 protein in the intestinal cells of the individual.

The present invention is further summarized in that a method is described for reducing cholesterol transport from the gut into the blood or lymph comprising administering a modulator of the ABC1 protein. In a preferred embodiment, the modulator is an inhibitor of ABC1 activity, and it is administered orally.

The present invention is also summarized in that a method for screening drug candidates for lowering serum LDL levels or for reducing cholesterol transport from the gut into the blood or lymph includes the steps of screening compounds for the effect of modulating ABC1 protein activity. In a preferred embodiment, the modulator is an inhibitor of ABC1 activity. In a further embodiment, successful candidates are further screened for the effect of not stimulating insulin production. Successful drug candidates may optionally be further modified by combinatorial chemistry to generate preferred therapeutic agents.

Compositions of the invention include compounds which are useful for reducing cholesterol transport from the gut to the blood or lymph and for the regulation and treatment of cardiovascular disorders (such as high LDL or serum cholesterol levels), obesity, elevated body-weight index and other disorders relating to lipid metabolism which are identified using the screening assays of the invention.

Other objects, advantages and features of the present invention will become apparent from the following specification.

BRIEF DESCRIPTION OF THE DRAWING FIGURES

DETAILED DESCRIPTION OF THE INVENTION

Figure 1:
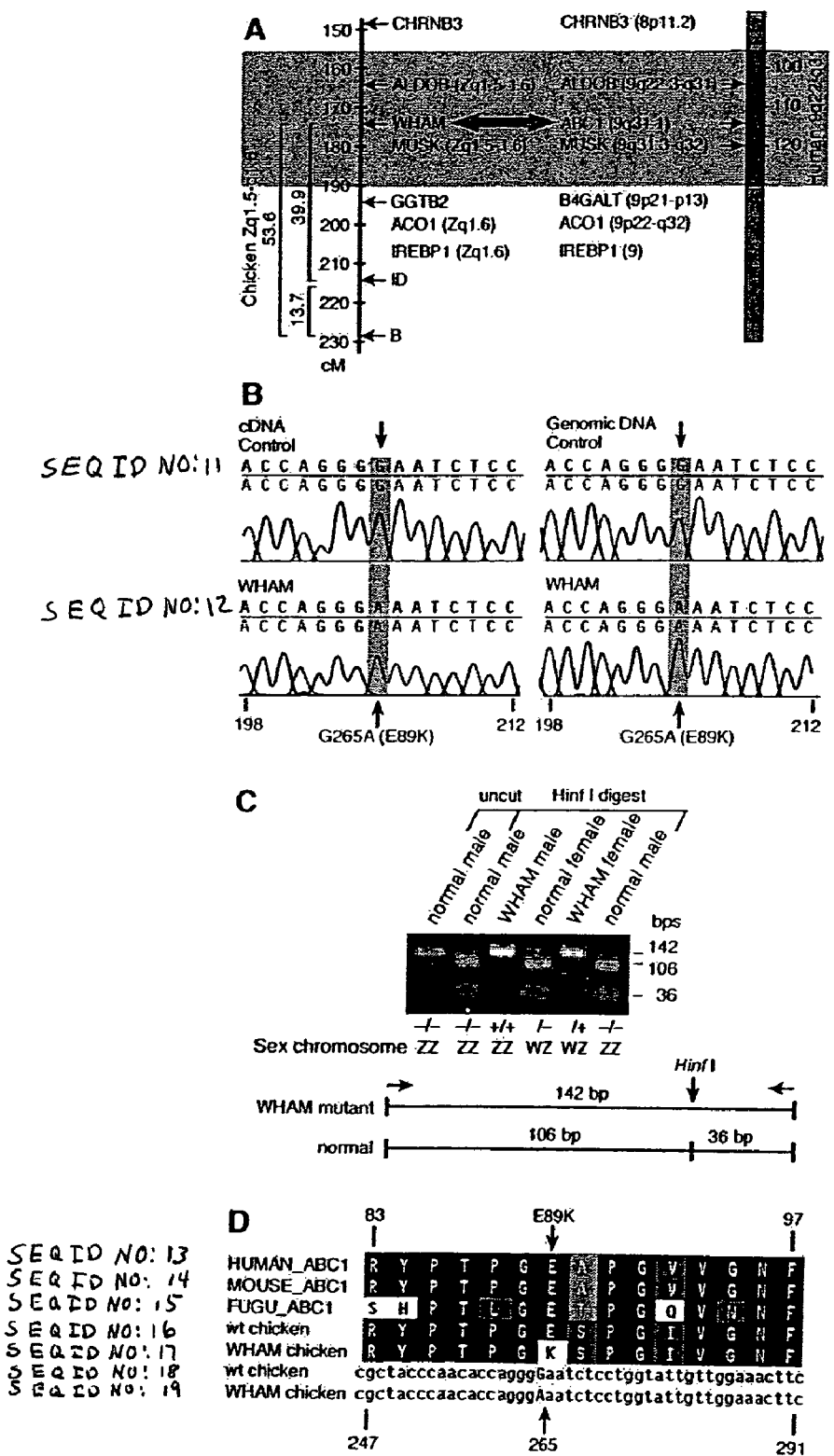
FIG. 1 is a graphical illustration of the relationship between the human ABC1 gene and the mutation responsible for the phenotype of the WHAM chickens.

The insights that gave rise to the present invention derive from several sources. One is the recent identification by several of the inventors of the specific human gene responsible for Tangier disease. That gene was identified to be a gene known as ABC1, a gene that is part of the ATP-binding cassette superfamily of genes. Deficiencies in the function of this gene are associated with decreased transport of cholesterol out of cells that synthesize excess cholesterol. The second insight was the understanding that the genetic mutation in the WHAM chickens is, in fact, a mutation in the same ABC1 gene or a related gene. This insight establishes for the first time that the ABC1 protein may be critical for cholesterol absorption. Because the mechanism of action of the mutant gene in the WHAM chickens had been previously understood to be a deficiency in absorption of isoprenoids and sterols from the lumen of the digestive tract, this observation suggested to the inventors that the same ABC1 gene may be necessary for cholesterol transport from the digestive tract to the blood stream. The combination of these two observations had led to the understanding, first expressed here, that lowered serum cholesterol levels, and in particular, lower levels of LDL, of "bad" cholesterol, can be achieved by blocking the transport action of the ABC1 in facilitating the transport of cholesterol from the intestinal lumen through the intestinal wall cells into the blood stream. Since it is revealed here that the ABC1 gene is a necessary component in the transport of isoprenoids and sterols from the gut into the blood stream, as revealed in particular by the inability of WHAM chickens to uptake these compounds from their diets, it also becomes clear that uptake of these compounds in healthy individuals from the intestines can also be inhibited by blocking the action of otherwise functional copies of this transport protein. Since cholesterol in the intestinal tract is either secreted by the liver into the bile and thus into the intestinal tract, or derives from exogenous sources, blocking the absorption of cholesterol from the gut into the blood stream through the intestinal wall will result in lowering the total level of cholesterol in the plasma of the individual.

The ABC1 protein is a cross-membrane transport protein. In cells throughout the body, the protein transports cholesterol from the cytosol into the blood stream. In the cells of the intestinal wall, this transport protein performs a similar function. Cholesterol is absorbed from the intestinal lumen into the cells lining the intestinal wall and is then transported into the blood stream. In the absence of an effective ABC1 protein, the cholesterol can not be transported into the blood or lymph and can go no further. Thus, in ABC1 deficient individuals, cholesterol accumulates in the wall of the intestines. In individuals with normal ABC1 protein function, the ABC1 protein serves to transport the cholesterol absorbed from the intestine from the cell into the blood stream. Thus inhibiting the transport function of the ABC1 protein in intestinal wall cells prevents cholesterol entering the gut from being transported into the blood stream.

This invention establishes for the first time the presence of a two stage process for cholesterol absorption from the gut: cholesterol first proceeds to cross the epithelial cells; and secondly by an ABC1-dependent process cholesterol is transported through the lamina propria into the blood or lymph. Thus an important aspect of this invention is the identification of a layer of cells beneath the columnar epithelium which are an essential part of the cholesterol absorption/transport pathway. These cells can be studied for other mechanisms or sites of activity for compounds which lead to inhibition of cholesterol absorption/transport from the gut to the blood.

This insight leads to other useful processes. Since the same gene, ABC1, is responsible for transport of cholesterol, phospholipids and other isoprenoids, including carotenoids, from intestinal wall cells into the blood stream, assays for the ability of a patient to transport of carotenoids from the gut into the serum will also be diagnostic of that person's ability to similarly transport cholesterol. Since mutations in ABC1 are a major cause of FHA, the carotenoid absorption test might constitute a clinically useful diagnostic procedure for identifying patients with ABC1 mutations and thus categorize patients for subsequent therapy.

The identification of a mutation in the ABC1 gene as the cause for Tangier disease was first reported only recently. See Brooks-Wilson et al. *Nature Genetics* 22:336–345 (1999), Bodzioch et al. *Nature Genetics* 22:347–351 (1999), and Rust et al. *Nature Genetics* 22:352–355, (1999), each of which is hereby incorporated by reference. The ABC1 protein is a complex membrane protein with twelve transmembrane domains, that is a part of the ABC gene family, whose members include proteins implicated in the active transport of substances across biological membranes. The papers cited in this paragraph established the role of the ABC1 transporter gene as a necessary agent for the transport of cholesterol out across the membrane of a cholesterol producing cell. This document is the first report of the observation that the ABC1 gene is also necessary for the transport of cholesterol from the intestines to the blood stream and to teach a method to make use of that knowledge for human health purposes.

The establishment of the role for the ABC1 transporter protein in cholesterol uptake was made on the basis of the WHAM chickens, following the identification of the ABC1 gene as the causative agent for Tangier disease. It had been previously known that the mutant gene responsible for the mutant phenotype in the chickens mapped to the Z sex chromosome, in the Y locus and proximal to the ID locus. Examination of the public mapping data from the chicken genome mapping project showed a region of synteny with a region of human chromosome 9 in which the human ABC1 gene is present. In short, genetic mapping has demonstrated that genes from syntenic loci are responsible for the mutation in the WHAM chickens and in the Tangier patients. DNA sequence anlysis has identified the mutation in the chicken ABC1 gene causitive of HDL deficiency. In the WHAM chickens, however, the symptoms appear to also be the result of deficiencies in uptake of substances (i.e. cholesterol and carotenoids) from the digestive tract. In the WHAM chicken, cholesterol ester accumulates in the wall of the intestine, but not in the columnar epithelium, rather in the lamina propria. ABC1 mRNA is present in this region in control chickens but is not seen in the columnar epithelium. This establishes the utility of the WHAM chickens as an animal model for the study of HDL and cholesterol transport deficiency in humans, and also provides the basis for the therapeutic and diagnostic strategies described in this document.

The WHAM chicken has thus supplied the first genetic evidence that vertebrates, like invertebrates, have an extracellular lipoprotein assembly pathway. Since the WHAM chickens are refractive to the effects of a high-cholesterol diet (see Examples, below), the inventors concluded that ABC1 plays a role in intestinal cholesterol transport.

The first and potentially most important strategy described here is based on the fact that if ABC1 is necessary for the transport of cholesterol from the intestines into the blood stream. Blocking the action of the ABC1 gene or protein in the cells of the intestinal wall from performing that transport activity results in decreasing the transport of cholesterol into the serum. Cholesterol normally enters the intestinal lumen from two sources, food eaten by the individual and from cholesterol excreted from the liver into the bile. If cholesterol transport is inhibited in the intestinal wall cells by an ABC1 blocker, serum cholesterol levels will go down, since the cholesterol secreted by the liver will not be re-directed into the blood stream. On the other hand, if the inhibition of cholesterol uptake is selectively performed only in the cells of the intestinal wall, there should be no effect on the levels of HDL in the individual's serum, since the normal transport of cholesterol out of cholesterol producing cells will not be affected. Since the site of ABC1 activity that is to be blocked is in the cells of the intestinal wall, and blockage of ABC1 activity elsewhere may not be desirable, it is envisioned that the most convenient mode of delivery of the ABC1 blocker will be by oral delivery.

It is envisioned that the transport activity of ABC1 can be inhibited in many ways. One method would be to inhibit the expression of endogenous ABC1 gene activity to reduce the abundance of the ABC1 protein. An example of the implementation of this method would be an antisense construct for the ABC1 gene delivered (either in free form or by liposome or viral vector) through the intestinal tract to the intestinal wall cells. Another method would be to inhibit the activity of the protein by introducing a chemical inhibitor of the activity of the protein. An example of the second method would be the use of a drug containing a sulfonylurea compound, an agent known to inhibit ABC1 protein activity. In either case, the delivery methodology should be on capable of delivering the inhibiting agent to the cells of the intestinal lining.

For the modulation of the activity of ABC1 using genetic techniques, it is necessary to introduce the genetic elements into the cells of the intestinal epithelium. This can be done by using liposomes of viral vectors carrying the genetic elements orally. Such liposomes or viral vectors can achieve transfection of foreign genetic constructs into the somatic cells with which they come in contact as some frequency dependent on the efficiency of the particular vector. There are several methods that can be used to inhibit gene activity, but amongst those the best known is based on the used of an antisense RNA construct. A genetic construct can be made which encodes the coding region of at least a portion of the coding region of the native ABC1 gene, in the antisense direction. When such a construct is expressed in cells, the antisense RNA produced interferes with normal gene expression activity in the cells and the native levels of the targeted protein drop. Such an antisense technique can be used to selectively target unwanted cholesterol transport activity in the intestinal lining without interfering with desired ABC1 activity throughout the rest of the body. The sequence of the human ABC1 gene is appended hereto as SEQ ID:NO: 1 to enable the implementation of this strategy.

The sulfonylurea drugs act to inhibit ABC1. For example, one member of this drug family, glibenclamide, has been shown to inhibit iodide transport in frog oocytes which are induced to express ABC1. Becq et al. *Jour. Biol. Chem.* 272:5:2695–2699 (1997). Sulfonylurea drugs are also currently used in the treatment of diabetes to stimulate insulin secretion from islet cells in the pancreas. It is preferred that the sulfonylurea drug be one that is highly inhibitory of ABC1 activity but not one that stimulates insulin production. In this way, the drug could interfere with cholesterol uptake without unnecessarily stimulating insulin production. It is specifically envisioned that the family of sulfonylurea compounds can be screened to identify those members of the group which retain the ability to inhibit the activity of ABC1 without stimulating the production of insulin. The outline of a methodology for that screening process is described below.

Another use for the observation that the mutation in the ABC1 gene in the cause for the phenotype in the WHAM chickens arises from the observation that the WHAM chickens were originally identified primarily because they cannot extract carotenoids from their gut, leaving the animals deficient in carotene (as a result, their serum is colorless instead of yellow and their skin is white instead of yellow).

Also, with the insight into the intestinal transport function of the ABC1 gene disclosed here, it becomes possible to screen new drugs for cholesterol lowering function. Chemical entities that will bind with high affinity to the extracellular domains of the ABC1 protein, such as domains identified above, will prove to have cholesterol lowering properties as long as they are capable of passing through the stomach into the intestines without deactivation or digestion. It is then possible to use the WHAM chickens as a control to test drugs identified in this fashion, since such drug should be ineffective in these chickens.

Another specifically envisioned class includes of inhibitors of ABC1 is antibodies, polyclonal or monoclonal, which are directed against the appropriate domains of the ABC1 transporter protein which are located on the surface of the intestinal cells. For the approach of using antibodies, it is preferred that the antibodies be raised against the domains of the ABC1 protein which appear to be exposed on the surfaces of those cells. Set forth in the sequence listing at the end of this document is the complete DNA sequence for the ABC1 gene and the amino acid sequence for the ABC1 transporter protein. The domains of the transported protein that are located exposed on the surface of the epithelial cells in the intestinal wall can be predicted based on computer analysis of this sequence information. The putative external domains of the ABC1 transporter protein identified by this means are set forth in the list following this paragraph. It is predicted that these regions are essential for the transport function of the ABC1 protein and that a protein or small molecule which binds to one of these regions (or to any other essential region of the ABC1 protein) will inhibit the transport activity of ABC1. To make antibodies against these regions, peptides can be prepared that include the amino acids sequences of these regions. These peptides can be used to make polyclonal antibodies by immunizing animals and recovering their serum. Monoclonal antibodies can be made as well. It is also envisaged that antibodies can be made by injecting the peptides into chickens and thus these chickens will produce eggs enriched in the needed antibody as in Yokoyama et al. *Am. J. Vet. Res.* 54:6:876–872 (1993). The antibodies can be recovered from the egg yolks and prepared separately, or the eggs themselves can be eaten by a patient, to expose the antibody to the target, i.e. the exposed domains of the ABC1 transporter protein. It is specifically envisaged that the resulting antibodies may be ingested by the individual being treated for introduction to the target site. It has been previously demonstrated that antibodies may be introduced into an individual's food source to have selected effects on intestinal receptors, as is demonstrated by U.S. Pat. Nos. 5,814,361 and 5,725,873, the specifications of which are hereby incorporated by reference. These patents disclose suitable methods for the delivery of antibodies in the diet to individuals to block an intestinal hormone.

Predicted External Domains of ABC1

TM1–TM2 (SEQ ID NO:3): 663 KEARLKETMRIMGLDNSI 680

TM3–TM4 (SEQ ID NO:4): 740 FSRAN 744

TM5–TM6 (SEQ ID NO:5): 795 ALFEEQGIGVQWDNLFESPVEEDGFN 820

TM7–TM8 1371

(SEQ ID NO:6):

FGKYPSLELQPWMYNEQYT-
FVSNDAPEDTGTLELLNALTKDPGFGTR CMEG-
NPIPDTPCQAGEEEWTTAPVPQTIM-
DLFQNGNWTMQNPSPACQ
CSSDKIKKMLPVCPPGAGGLPPPQRKQN-
TADILQDLTGRNISDYLVKT YVQIIAKSLKNKI-
WVNEFRYGGFSLGVSNTQALPPSQEVN-
DAIKQMKK
HLKLAKDSSADRFLNSLGRFMTGLDTRN-
NVKVWFNNKGWHAISSFLN VINNAILRANLQK-
GENPSHYGITAFNHPLNLTKQQLSEVALMTTSVD
1654

TM9–TM10 (SEQ ID NO:7): 1741 LLLLYGWSITPLMYPASFVFKIP 1763

TH11–TH12 (SEQ ID NO:8): 1823 VKNQAMADAL-
ERFGENRFVSPLSW

DLVGR 1851

ABC1 Nomenclature and Reported Nucleic Acid/Protein Sequences

The ABC1 gene and protein referred to herein is also sometimes referred to as ABCA1 or CERP (cholesterol-efflux regulatory protein) in the scientific literature. The complete ABCA1 cDNA, genomic DNA sequence, and predicted protein sequence has been disclosed in PCT/IBOO/00532 and U.S. patent application Ser No. 09/654,328, filed Sep. 1, 2000, incorporated herein by reference. The human ABCA1 in the GeneBank has the following accession numbers: AJ012376; AF165281; NM_005502; AF285167. Corresponding ABCA1 genes and peptides from other organisms have also been reported in GenBank.

Screening Assays for Modulators of ABC1 Activity

The invention provides screening assay methods for identifying therapeutic compounds useful for treatments which reduce exogenous cholesterol transport from the gut lumen to the blood or lymph and for the regulation and treatment of cardiovascular disorders (such as high LDL or serum cholesterol levels), obesity, elevated body-weight index and other disorders relating to lipid metabolism which can be used in human patients. The screening assay methods of the invention simplify the evaluation, identification and development of candidate compounds and therapeutic agents for the treatment of such conditions and disorders. In general, the screening methods provide a simplified means for selecting natural product extracts or compounds of interest from a large population, generally a compound library, which are further evaluated and condensed to a few active and selective materials useful for treatments of such conditions and disorders (these treatments are sometimes referred to herein as the "desired purposes of the invention"). Constituents of this pool are then purified, evaluated, or modified by combinatorial chemistry in order to identify preferred compounds for the desired purposes of the invention.

Compounds that modulate ABC1 biological activity can be identified by their effects on a known biological activity of ABC1, including but not limited to cellular or microsomal scale assays of efflux of phospholipid, cholesterol or other chemical species, protein level assays of binding specificity, protein stability, regulated catabolism, or its ability to bind proteins, lipids or other factors, expression level or stability of ABC1 mRNA and precursor RNAs, or, in short, by any activity that identifies a biological effect, characteristic or feature of the ABC1 protein.

What follows is a general description of potential ABC1 screening assay. More detailed descriptions of certain of these assays are set out in a separate section below.

In one example, the phosphorylation state or other post-translational modification is monitored as a measure of ABC1 biological activity. ABC1 has ATP binding sites, and thus assays may wholly or in part test the ability of ABC1 to bind ATP or to exhibit ATPase activity. Drug screening assays could be based upon assaying for the ability of the protein to form a channel, or upon the ability to transport cholesterol or another molecule, or based upon the ability of other proteins bound by or regulated by ABC1 to form a channel. In addition to its role as a regulator of cholesterol levels, ABC1 may also transports anions. Functional assays could be based upon this property, and could employ drug screening technology such as (but not limited to) the ability of various dyes to change color in response to changes in specific ion concentrations in such assays can be performed in vesicles such as liposomes, or adapted to use whole cells.

Drug screening assays can also be based upon the ability of ABC1 or other ABC transporters to interact with other proteins. Such interacting proteins can be identified by a variety of methods known in the art, including, for example, radioimmunoprecipitation, co-immunoprecipitation, co-purification, and yeast two-hybrid screening. Such interactions can be further assayed by means including but not limited to fluorescence polarization or scintillation proximity methods. Drug screens can also be based upon functions of the ABC1 protein deduced upon X-ray crystallography of the protein and comparison of its 3-D structure to that of proteins with known functions. Such a crystal structure has been determined for the prokaryotic ABC family member HisP, histidine permease. Drug screens can be based upon a function or feature apparent upon creation of a transgenic or knock-out mouse, or upon overexpression of the protein or protein fragment in mammalian cells in vitro. Moreover, expression of mammalian (e.g., human) ABC1 in yeast or *C. elegans* allows for screening of candidate compounds in wild-type and mutant backgrounds, as well as screens for mutations that enhance or suppress an ABC1-dependent phenotype. Modifier screens can also be performed in ABC1 transgenic or knock-out mice.

Additionally, drug screening assays can also be based upon ABC1 functions deduced upon antisense interference with the gene function. Intracellular localization of ABC1, or effects which occur upon a change in intracellular localization of the protein, can also be used as an assay for drug screening. Immunocytochemical methods will be used to determine the exact location of the ABC1 protein.

Human and rodent ABC1 protein can be used as an antigen to raise antibodies, including monoclonal antibodies. Such antibodies will be useful for a wide variety of purposes, including but not limited to functional studies and the development of drug screening assays and diagnostics. Monitoring the influence of agents (e.g., drugs, compounds) on the expression or biological activity of ABC1 can be applied not only in basic drug screening, but also in clinical trials. For example, the effectiveness of an agent determined by a screening assay as described herein to decrease ABC1 gene expression, protein levels, or biological activity can be monitored in clinical trails of subjects exhibiting altered ABC1 gene expression, protein levels, or biological activity. Alternatively, the effectiveness of an agent determined by a screening assay to modulate ABC1 gene expression, protein levels, or biological activity can be monitored in clinical trails of subjects exhibiting decreased altered gene expression, protein levels, or biological activity. In such clinical trials, the expression or activity of ABC1 and, preferably, other genes that have been implicated in, for example, cardiovascular disease can be used to ascertain the effectiveness of a particular drug.

For example, and not by way of limitation, genes, including ABC1, that are modulated in cells by treatment with an agent (e.g., compound, drug or small molecule) that modulates ABC1 biological activity (e.g., identified in a screening assay as described herein) can be identified. Thus, to study the effect of agents on reducing cholesterol transport from the gut to the blood or lymph, or for reducing LDL or serum cholesterol levels, for example, in a clinical trial, cells can be isolated and RNA prepared and analyzed for the levels of expression of ABC1 and other genes implicated in the disorder. The levels of gene expression can be quantified by Northern blot analysis or RT-PCR, or, alternatively, by measuring the amount of protein produced, by one of a number of methods known in the art, or by measuring the levels of biological activity of ABC1 or other genes. In this way, the gene expression can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ABC1 protein, mRNA, or genomic DNA in the preadministration sample; (iii) obtaining one or more post-administration samples from the subject; (iv) detecting the level of expression or activity of the ABC1 protein, mRNA, or genomic DNA in the post-administration samples; (v) comparing the level of expression or activity of the ABC1 protein, mRNA, or genomic DNA in the pre-administration sample with the ABC1 protein, mRNA, or genomic DNA in the post administration sample or samples; and (vi) altering the administration of the agent to the subject accordingly. For example, administration of the agent may be desirable to decrease the expression or activity of ABC1.

The ABC1 gene or a fragment thereof can be used as a tool to express the protein in an appropriate cell in vitro or in vivo (gene therapy), or can be cloned into expression vectors which can be used to produce large enough amounts of ABC1 protein to use in in vitro assays for drug screening. Expression systems which may be employed include baculovirus, herpes virus, adenovirus, adeno-associated virus, bacterial systems, and eucaryotic systems such as CHO cells. Naked DNA and DNA-liposome complexes can also be used.

Assays of ABC1 activity includes binding to intracellular interacting proteins; interaction with a protein that modulates ABC1 activity; interaction with HDL particles or constituents; interaction with other proteins which facilitate interaction with HDL or its constituents; and measurement of cholesterol efflux. Furthermore, assays may be based upon the molecular dynamics of macromolecules, metabolites and ions by means of fluorescent-protein biosensors.

Alternatively, the effect of candidate modulators on expression or activity may be measured at the level of ABC1 protein production using the same general approach in combination with standard immunological detection techniques, such as Western blotting or immunoprecipitation with an ABC1-specific antibody. Again, useful modulators are identified as those which produce a change in ABC1 polypeptide production. Agonists may also affect ABC1 activity without any effect on expression level.

Agonists, antagonists, or mimetics found to be effective at modulating the level of cellular ABC1 expression or activity may be confirmed as useful in animal models (for example, mice, pigs, rabbits, or chickens).

A compound that promotes a decrease in ABC1 expression or activity is considered particularly useful in the invention; such a molecule may be used, for example, as a therapeutic to decrease the level or activity of native, cellular ABC1 and thereby reduce cholesterol transport from the gut to the blood or lymph, or reduce LDL or serum cholesterol levels in an animal (for example, a human).

One method for decreasing ABC biological activity is to decrease the stabilization of the ABC protein or to prevent its degradation.

In one example, cells expressing an ABC1 polypeptide having a mutation are transiently metabolically labeled during translation and the half-life of the ABC1 polypeptide is determined using standard techniques. Mutations that decrease the half-life of an ABC1 polypeptide are ones that decrease ABC1 protein stability.

The Cholesterol Efflux Assay as a Drug Screen

A cholesterol efflux assay measures the ability of cells to transfer cholesterol to an extracellular acceptor molecule and is dependent on ABC1 function. A standard cholesterol efflux assay is set out in Marcil et al., *Arterioscler. Thromb. Vasc. Biol.* 19:159–169, 1999, incorporated by reference herein for all purposes. Prior to this invention, this assay has not been used to identify compounds useful for reducing cholesterol transport from the gut to the blood or lymph, or for reducing LDL or serum cholesterol levels.

In this procedure, cells are loaded with radiolabeled cholesterol by any of several biochemical pathways. Cholesterol efflux of cells is measured after incubation for various times (typically 0 to 24 hours) in the presence of HDL3 or purified ApoAI. Cholesterol efflux is determined as the percentage of total cholesterol in the culture medium after various times of incubation. Increased ABC1 expression levels and/or biological activity are associated with increased efflux while decreased levels of ABC1 expression and/or biological activity are associated with decreased cholesterol efflux.

This assay can be readily adapted to the format used for drug screening, which may consist of a multi-well (e.g., 96-well) format. Modification of the assay to optimize it for drug screening would include scaling down and streamlining the procedure, modifying the labeling method, using a different cholesterol acceptor, altering the incubation time, and changing the method of calculating cholesterol efflux. In all these cases, the cholesterol efflux assay remains conceptually the same, though experimental modifications may be made.

For high throughput, fluorescent lipids can be used to measure ABC1-catalyzed lipid efflux. For phospholipids, a fluorescent precursor, C6-NBD-phosphatidic acid, can be used. This lipid is taken up by cells and dephosphorylated by phosphatidic acid phosphohydrolase. The product, NBD-diglyceride, is then a precursor for synthesis of glycerophospholipids like phosphatidylcholine. The efflux of NBD-phosphatidylcholine can be monitored by detecting fluorescence resonance energy transfer (FRET) of the NBD to a suitable acceptor in the cell culture medium. This acceptor can be rhodamine-labeled phosphatidylethanolamine, a phospholipid that is not readily taken up by cells. The use of short-chain precursors obviates the requirement for the phospholipid transfer protein in the media. For cholesterol, NBD-cholesterol ester can be reconstituted into LDL. The LDL can efficiently deliver this lipid to cells via the LDL receptor pathway. The NBD-cholesterol esters are hydrolyzed in the lysosomes, resulting in NBD-cholesterol that can now be transported back to the plasma membrane and efflux from the cell. The efflux can be monitored by the aforementioned FRET assay in which NBD transfers its fluorescence resonance energy to the rhodamine-phosphatidylethanoline acceptor.

Protein-Based Assays

ABC1 polypeptide (purified or unpurified) can be used in an assay to determine its ability to bind another protein (including, but not limited to, proteins found to specifically interact with ABC1). The effect of a compound on that binding is then determined. Useful ABC1 proteins include wild-type and mutant ABC1 proteins or protein fragments, in a recombinant form or endogenously expressed.

Protein Interaction Assays

ABC1 protein (or a polypeptide fragment thereof or an epitope-tagged form or fragment thereof) is harvested from a suitable source (e.g., from a prokaryotic expression system, eukaryotic cells, a cell-free system, or by immunoprecipitation from ABC1-expressing cells). The ABC1 polypeptide is then bound to a suitable support (e.g., nitrocellulose or an antibody or a metal agarose column in the case of, for example, a his-tagged form of ABC1). Binding to the support is preferably done under conditions that allow proteins associated with ABC1 polypeptide to remain associated with it. Such conditions may include use of buffers that minimize interference with protein-protein interactions. The binding step can be done in the presence and absence of compounds being tested for their ability to interfere with interactions between ABC1 and other molecules. If desired, other proteins (e.g., a cell lysate) are added, and allowed time to associate with the ABC polypeptide. The immobilized ABC1 polypeptide is then washed to remove proteins or other cell constituents that may be non-specifically associated with it the polypeptide or the support. The immobilized ABC1 polypeptide is then dissociated from its support, and so that proteins bound to it are released (for example, by heating), or, alternatively, associated proteins are released from ABC1 without releasing the ABC1 polypeptide from the support. The released proteins and other cell constituents can be analyzed, for example, by SDS-PAGE gel electrophoresis, Western blotting and detection with specific antibodies, phosphoamino acid analysis, protease digestion, protein sequencing, or isoelectric focusing. Normal and mutant forms of ABC1 can be employed in these assays to gain additional information about which part of ABC1 a given factor is binding to. In addition, when incompletely purified polypeptide is employed, comparison of the normal and mutant forms of the protein can be used to help distinguish true binding proteins.

The foregoing assay can be performed using a purified or semipurified protein or other molecule that is known to interact with ABC1. This assay may include the following steps.

1. Harvest ABC1 protein and couple a suitable fluorescent label to it;

2. Label an interacting protein (or other molecule) with a second, different fluorescent label. Use dyes that will produce different quenching patterns when they are in close proximity to each other vs. when they are physically separate (i.e., dyes that quench each other when they are close together but fluoresce when they are not in close proximity);

3. Expose the interacting molecule to the immobilized ABC1 in the presence or absence of a compound being tested for its ability to interfere with an interaction between the two; and 4. Collect fluorescent readout data.

Another possible assay is the Fluorescent Resonance Energy Transfer (FRET) assay. This assay can be performed as follows.

1. Provide ABC1 protein or a suitable polypeptide fragment thereof and couple a suitable FRET donor (e.g., nitro-benzoxadiazole (NBD)) to it;

2. Label an interacting protein (or other molecule) with a FRET acceptor (e.g., rhodamine);

3. Expose the acceptor-labeled interacting molecule to the donor-labeled ABC1 in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

Membrane Permeability Assay

The ABC1 protein can also be tested for its effects on membrane permeability. For example, beyond its putative ability to translocate lipids, ABC1 might affect the permeability of membranes to ions. Other related membrane proteins, most notably the cystic fibrosis transmembrane conductance regulator and the sulfonylurea receptor, are associated with and regulate ion channels.

ABC1 or a fragment of ABC1 is incorporated into a synthetic vesicle, or, alternatively, is expressed in a cell and vesicles or other cell sub-structures containing ABC1 are isolated. The ABC1-containing vesicles or cells are loaded with a reporter molecule (such as a fluorescent ion indicator whose fluorescent properties change when it binds a particular ion) that can detect ions (to observe outward movement), or alternatively, the external medium is loaded with such a molecule (to observe inward movement). A molecule which exhibits differential properties when it is inside the vesicle compared to when it is outside the vesicle is preferred. For example, a molecule that has quenching properties when it is at high concentration but not when it is at another low concentration would be suitable. The movement of the charged molecule (either its ability to move or the kinetics of its movement) in the presence or absence of a compound being tested for its ability to affect this process can be determined.

In another assay, membrane permeability is determined electro-physiologically by measuring ionic influx or efflux mediated by or modulated by ABC1 by standard electro-physiological techniques. A suitable control (e.g., TD cells or a cell line with very low endogenous ABC1 expression) can be used as a control in the assay to determine if the effect observed is specific to cells expressing ABC1.

In still another assay, uptake of radioactive isotopes into or out of a vesicle can be measured. The vesicles are separated from the extravesicular medium and the radioactivity in the vesicles and in the medium is quantitated and compared.

Nucleic Acid-Based Assays

ABC1 nucleic acid may be used in an assay based on the binding of factors necessary for ABC1 gene transcription. The association between the ABC1 DNA and the binding factor may be assessed by means of any system that discriminates between protein-bound and non-protein-bound DNA (e.g., a gel retardation assay). The effect of a compound on the binding of a factor to ABC1 DNA is assessed by means of such an assay. In addition to in vitro binding assays, in vivo assays in which the regulatory regions of the ABC1 gene are linked to reporter genes can also be performed.

Assays Measuring Stability of ABC1 Protein or mRNA

A cell-based or cell-free system can be used to screen for compounds based on their effect on the half-life of ABC1 mRNA or ABC1 protein. The assay may employ labeled mRNA or protein. Alternatively, ABC1 mRNA may be detected by means of specifically hybridizing probes or a quantitative PCR assay. Protein can be quantitated, for example, by fluorescent antibody-based methods.

In Vitro mRNA Stability Assay

1. Isolate or produce, by in vitro transcription, a suitable quantity of ABC1 mRNA;

2. Label the ABC1 mRNA;

3. Expose aliquots of the mRNA to a cell lysate in the presence or absence of a compound being tested for its ability to modulate ABC1 mRNA stability;

4. Assess intactness of the remaining mRNA at suitable time points.

In Vitro Protein Stability Assay

1. Express a suitable amount of ABC1 protein;

2. Label the protein;

3. Expose aliquots of the labeled protein to a cell lysate in the presence or absence of a compound being tested for its ability to modulate ABC1 protein stability;

4. Assess intactness of the remaining protein at suitable time points

In Vivo mRNA or Protein Stability Assay

1. Incubate cells expressing ABC1 mRNA or protein with a tracer (radiolabeled ribonucleotide or radiolabeled amino acid, respectively) for a very brief time period (e.g., five minutes) in the presence or absence of a compound being tested for its effect on mRNA or protein stability;

2. Incubate with unlabeled ribonucleotide or amino acid; and

3. Quantitate the ABC1 mRNA or protein radioactivity at time intervals beginning with the start of step 2 and extending to the time when the radioactivity in ABC1 mRNA or protein has declined by approximately 80%. It is preferable to separate the intact or mostly intact mRNA or protein from its radioactive breakdown products by a means such as gel electrophoresis in order to quantitate the mRNA or protein.

Assays Measuring Inhibition of Dominant Negative Activity

Mutant ABC1 polypeptides are likely to have dominant negative activity (i.e., activity that interferes with wild-type ABC1 function). An assay for a compound that can interfere with such a mutant may be based on any method of quantitating normal ABC1 activity in the presence of the mutant. For example, normal ABC1 facilitates cholesterol efflux, and a dominant negative mutant would interfere with this effect. The ability of a compound to counteract the effect of a dominant negative mutant may be based on cellular cholesterol efflux, or on any other normal activity of the wild-type ABC1 that was inhibitable by the mutant.

Assays Measuring Phosphorylation

The effect of a compound on ABC1 phosphorylation can be assayed by methods that quantitate phosphates on proteins or that assess the phosphorylation state of a specific residue of a ABC1. Such methods include but are not limited to $^{32}P$ labelling and immunoprecipitation, detection with antiphosphoamino acid antibodies (e.g., antiphosphoserine antibodies), phosphoamino acid analysis on 2-dimensional TLC plates, and protease digestion fingerprinting of proteins followed by detection of $^{32}P$-labeled fragments.

Assays Measuring Other Post-Translational Modifications

The effect of a compound on the post-translational modification of ABC1 is based on any method capable of quantitating that particular modification. For example, effects of compounds on glycosylation may be assayed by treating ABC1 with glycosylase and quantitating the amount and nature of carbohydrate released.

Assays Measuring ATP Binding

The ability of ABC1 to bind ATP provides another assay to screen for compounds that affect ABC1. ATP binding can be quantitated as follows.

1. Provide ABC1 protein at an appropriate level of purity and reconsititute it in a lipid vesicle;

2. Expose the vesicle to a labeled but non-hydrolyzable ATP analog (such as gamma $^{35}S$-ATP) in the presence or absence of compounds being tested for their effect on ATP binding. Note that azido-ATP analogs can be used to allow covalent attachment of the azido-ATP to protein (by means of U.V. light), and permit easier quantitation of the amount of ATP bound to the protein.

3. Quantitate the amount of ATP analog associated with ABC1

Assays Measuring ATPase Activity

Quantitation of the ATPase activity of ABC1 can also be assayed for the effect of compounds on ABC1. This is preferably performed in a cell-free assay so as to separate ABC1 from the many other ATPases in the cell. An ATPase assay may be performed in the presence or absence of membranes, and with or without integration of ABC1 protein into a membrane. If performed in a vesicle-based assay, the ATP hydrolysis products produced or the ATP hydrolyzed may be measured within or outside of the vesicles, or both. Such an assay may be based on disappearance of ATP or appearance of ATP hydrolysis products. For high-throughput screening, a coupled ATPase assay is preferable. For example, a reaction mixture containing pyruvate kinase and lactate dehydrogenase can be used. The mixture includes phosphoenolpyruvate (PEP), nicotinamide adenine dinucleotide (NAD+), and ATP. The ATPase activity of ABC1 generates ADP from ATP. The ADP is then converted back to ATP as part of the pyruvate kinase reaction. The product, pyruvate, is then converted to lactate. The latter reaction generates a colored quinone (NADH) from a colorless substrate (NAD+), and the entire reaction can be monitored by detection of the color change upon formation of NADH. Since ADP is limiting for the pyruvate kinase reaction, this coupled system precisely monitors the ATPase activity of ABC1.

Animal Model Systems

Compounds identified as having activity in any of the above-described assays are subsequently screened in any available animal model system, including, but not limited to, pigs, rabbits, and WHAM chickens. Test compounds are administered to these animals according to standard methods. Test compounds may also be tested in mice bearing mutations in the ABC1 gene. Additionally, compounds may be screened for their ability to enhance an interaction between ABC1 and any HDL particle constituent such as ApoAI, ApoAII, or ApoE.

Knock-Out Mouse Model

An animal, such as a mouse, that has had one or both ABC1 alleles inactivated (e.g., by homologous recombination) is a preferred animal model for screening for compounds that reduce exogenous cholesterol transport from the gut lumen to the blood or lymph and for the regulation and treatment of cardiovascular disorders (such as high LDL or serum cholesterol levels), obesity, elevated body-weight index and other disorders relating to lipid metabolism. Such an animal can be produced using standard techniques. In addition to the initial screening of test compounds, the animals having mutant ABC1 genes are useful for further testing of efficacy and safety of drugs or agents first identified using one of the other screening methods described herein. Cells taken from the animal and placed in culture can also be exposed to test compounds.

WHAM Chickens: an Animal Model for Low HDL Cholesterol

Wisconsin Hypo-Alpha Mutant (WHAM) chickens arose by spontaneous mutation in a closed flock. Mutant chickens came to attention through their a Z-linked white shank and white beak phenotype referred to as 'recessive white skin' (McGibbon, 1981) and were subsequently found to have a profound deficiency of HDL (Poernama et al., 1990).

This chicken low HDL locus (Y) is Z-linked, or sex-linked. (In birds, females are ZW and males are ZZ). Genetic mapping placed the Y locus on the long arm of the Z chromosome (Bitgood, 1985), proximal to the ID locus (Bitgood, 1988). Examination of current public mapping data for the chicken genome mapping project, ChickMap (maintained by the Roslin Institute) showed that a region of synteny with human chromosome 9 lies on the long arm of the chicken Z chromosome (Zq) proximal to the ID locus. Evidence for this region of synteny is the location of the chicken aldolase B locus (ALDOB) within this region. The human ALDOB locus maps to chromosome 9q22.3 (The Genome Database), not far from the location of human ABC1. This comparison of maps showed that the chicken Zq region near chicken ALDOB and the human 9q region near human ALDOB represent a region of synteny between human and chicken.

We predicted that ABC1 is mutated in WHAM chickens. In support of this, we have identified an E to K mutation at a position that corresponds to amino acid 89 of human ABC1. This non-conservative substitution is at a position that is conserved among human, mouse, and chicken, indicating that it is in a region of the protein likely to be of functional importance.

Discovery of the WHAM mutation in the amino-terminal portion of the ABC1 protein also establishes the importance of the amino-terminal region. This region may be critical because of association with other proteins required to carry out cholesterol efflux or related tasks. It may be an important regulatory region (there is a phosphorylation site for casein kinase near the mutated residue), or it may help to dictate a precise topological relationship with cellular membranes (the N-terminal 60 amino acid region contains a putative membrane-spanning or membrane-associated segment).

The amino-terminal region of the protein (up to the first 6-TM region at approximately amino acid 639) is an ideal tool for screening factors that affect ABC1 activity. It can be expressed as a truncated protein in ABC1 wild type cells in order to test for interference of the normal ABC1 function by the truncated protein. If the fragment acts in a dominant negative way, it could be used in immunoprecipitations to identify proteins that it may be competing away from the normal endogenous protein.

The C-terminus also lends itself to such experiments, as do the intracellular portions of the molecule, expressed as fragments or tagged or fusion proteins, in the absence of transmembrane regions.

Since it is possible that there are several genes in the human genome which affect cholesterol efflux, it is important to establish that any animal model to be used for a human genetic disease represents the homologous locus in that animal, and not a different locus with a similar function. The evidence above establishes that the chicken Y locus and the human chromosome 9 low HDL locus are homologous. WHAM chickens are therefore an important animal model for the identification of drugs that modulate cholesterol efflux, and as such are useful for reducing cholesterol transport from the gut lumen to the blood or lymph and for the regulation and treatment of cardiovascular disorders (such as high LDL or serum cholesterol levels), obesity, elevated body-weight index and other disorders relating to lipid metabolism.

Compounds of the Invention

In general, novel compounds and therapeutic agents for reducing cholesterol transport from the gut lumen to the blood or lymph and for the regulation and treatment of cardiovascular disorders (such as high LDL or serum cholesterol levels), obesity, elevated body-weight index and other disorders relating to lipid metabolism are identified from large libraries of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Typically, a screening assay, such as a high throughput screening assay, will identify several or even many compounds which modulate the activity of the assay protein.

The compound identified by the screening assay may be further modified before it is used in humans as the therapeutic agent. Typically, combinatorial chemistry is performed on the modulator, to identify possible variants that have improved absorption, biodistribution, metabolism and/or excretion, or other important therapeutic aspects. The essential invariant is that the improved compounds share a particular active group or groups which are necessary for the desired modulation of the target protein. Many combinatorial chemistry techniques are well known in the art. Each one adds or deletes one or more constituent moieties of the compound to generate a modified analog, which analog is again assayed to identify compounds of the invention. Thus, as used in this invention, therapeutic compounds identified using an ABC1 screening assay of the invention include actual compounds so identified, and any analogs or combinatorial modifications made to a compound which is so identified which are useful for treatment of the disorders claimed herein.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their abilities in reducing cholesterol transport from the gut lumen to the blood or lymph and for the regulation and treatment of cardiovascular disorders (such as high LDL or serum cholesterol levels), obesity, elevated body-weight index and other disorders relating to lipid metabolism should be employed whenever possible.

When a crude extract is found to be capable of reducing cholesterol transport from the gut lumen to the blood or lymph and for the regulation and treatment of cardiovascular disorders (such as high LDL or serum cholesterol levels), obesity, elevated body-weight index and other disorders relating to lipid metabolism, further fractionation of the positive lead extract is necessary to isolate chemical constituent responsible for the observed effect. Thus, the goal of the extraction, fractionation, and purification process is the careful characterization and identification of a chemical entity within the crude extract having these desired activities. The same in vivo and in vitro assays described herein for the detection of activities in mixtures of compounds can be used to purify the active component and to test derivatives thereof. Methods of fractionation and purification of such heterogeneous extracts are known in the art. If desired, compounds shown to be useful agents for the treatment of pathogenicity are chemically modified according to methods known in the art. Compounds identified as being of therapeutic value are subsequently analyzed using any standard animal model for the desired disease or condition known in the art.

It is understood that compounds that indirectly modulate ABC1 activity, for example by modulation of proteins that modulate or are modulated by ABC1, may also be useful compounds for the desired purposes of the invention. Such compositions which are identified using the screening assays of this invention are also claimed.

Because one of the objects of the invention is to inhibit cholesterol transport in the gut but to not inhibit the assembly of HDL particles in peripheral tissues, certain features of preferred compositions of the invention can be identified. In particular, compositions which act locally in the gut or intestinal wall, but which do not circulate widely in the body are preferred. This object may be achieved with compounds which either are incapable of being transported by the blood or lymph or other extra-cellular fluid or particle. This object may also be achieved by obtaining compounds with limited in vivo stability (i.e. short half life upon oral administration) or which are subject to rapid metabolism to inert analogs after absorption by the intestinal wall.

As described previously, analogs of sulfonylureas are likely candidate compounds. However, sulfonylureas that are routinely used by diabetics are not useful in the invention to the extent that they cause the undesireable side-effect—in non-diabetic patients—of increased insulin secretion by the pancreas. Therefore, preferred compounds of the invention are inhibitors of ABC1 that either do not disperse significantly beyond the gut; do not cause unacceptable inhibition of ABC1 in peripheral tissues; and do not cause unacceptable side-effects.

Therapy Using Compositions of the Invention

Compositions of the invention, including but not limited to compounds that modulate biological activity or expression of ABC1 identified using any of the methods disclosed herein, or any preferred analogs of such compositions, may be administered with a pharmaceutically-acceptable diluent, carrier, or excipient, in unit dosage form. Conventional pharmaceutical practice may be employed to provide suitable formulations or compositions to administer such compositions to patients. Although oral administration is preferred, any appropriate route of administration may be employed, for example, intravenous, perenteral, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, Remington: *The Science and Practice of Pharmacy*, (19th ed.) ed. A. R. Gennaro Ark., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

A preferred embodiment for use of the compositions of the invention is for combination therapy employing a therapeutic agent of the invention which modulates or inhibits ABC1 activity in the gut in combination, simultaneous or sequential, with another agent which inhibits endogenous cholesterol synthesis, such as but not limited to a "statin" or HMGCoA reductase inhibitor, etc. This combination therapy is preferred in instances where inhibition of both exogenous cholesterol uptake from the gut and inhibition of endogenous cholesterol synthesis are desired. Therapeutic agents employed in this combination therapy are preferably oral compounds. In a preferred embodiment, the ABC1 inhibitor does not disperse beyond the lamina propria of the gut (i.e. it stays largely in the gut), whereas the inhibitor of endogenous cholesterol synthesis circulates to sites of endogenous cholesterol synthesis in the body.

EXAMPLES

WHAM Chickens.

The Wisconsin Mutant Hypoalpha (WHAM) chickens were discovered in 1981 in a flock of chickens maintained by the University of Wisconsin. The WHAM chickens have white skin and white beaks and have colorless rather than yellow serum, all due to the absence of carotenoids. The trait is inherited as a recessive sex-linked mutation on the Z-chromosome. These animals also have a severe deficiency of high density lipoprotein (HDL). Metabolic studies led to some degree of understanding of the defect in HDL metabolism. When $^{125}$I-labeled HDL particles were injected into WHAM chickens, their disappearance from the circulation was only moderately increase relative to normal chickens. However, when lipid-free $^{125}$I-apo-A1 was injected, it was removed from the circulation four-fold more rapidly in WHAM chickens compared to normal chickens, by the kidneys. Because apo-A1 synthesis and secretion is normal in the WHAM chickens, another factor had to affect the stability of apo-A1. Analysis of the serum phospholipids showed a 70% reduction, implying that the primary defect is in phospholipid efflux and demonstrated than an extracellular event is required for the formation of stable HDL particles.

The lipoprotein profiles of WHAM chicken and Tangier patient plasma show a similarly pronounced loss of HDL. IN addition, both plasma were found to show a decrease in plasma phospholipid levels. Two-dimensional thin-layer chromatography showed that the most pronounced phospholipid deficiency was in phosphotidylcholine and sphingomyelin.

A genetic study of the WHAM chicken genetic revealed that the location to which the mutant gene mapped adjacent to genes which in turn are adjacent to ABC1 on the human genome on chromosome 9. Shown in FIG. 1 is a map comparing the synteny between the WHAM mutation and the human ABC1 gene. Markers mapped genetically or physically are indicated by dashed arrows. Genes mapped only cytogenetically are positioned relative to other markers with the cytogenetic location in brackets.

To investigate the gene comparison, the coding region of the ABC1 genes from humans and the WHAM chickens were compared. The human and chicken genes are 78% identical at the nucleotide level and 85% identical (with 92% homology) at the amino acid level. The sequence of the normal and the WHAM chickens were identical with the exception of a G to an A transition in the WHAM DNA at nucleotide 265, corresponding to a glutamic acid to lysine substitution at amino acid position 89. Studies of the DNA of WHAM chickens, conducted by RFLP analysis, revealed that the mutation segregates with the phenotype of HDL deficiency.

Referring specifically again to FIG. 1, the WHAM mutation maps to a Z chromosome region syntenic to the 9q31.1 location of human ABC1. To the left is the chicken Z chromosome combined genetic and cytogenetic map. To the right is a combined human genetic and cytogenetic map. Positions of markers mapped genetically or physically are indicated by dashed arrows. Genes mapped only cytogenetically are positioned relative to other markers with the cytogenetic location in brackets. WHAM was genetically mapped relative to ID and B [the relative distances and the calculated WHAM-B distance are indicated, (1,2).]

At (B) in FIG. 1, the illustration conveys that the WHAM chicken ABC1 gene has a single amino acid substitution (E89K) relative to normal White Leghorn chicken. Total liver RNA from WHAM and normal male chickens was subjected to standard RT-PCR and sequencing methods (left panel) using primers corresponding to the cDNA sequences most conserved between human and mouse ABC1. The open reading frame (corresponding to amino acids 27 to 2261) was sequenced, revealed a single homozygous G to A transition in WHAM cDNA at position 265. (Numbering of nucleotides and amino acids is according to the new, longer open reading frame of human ABC1). The same alteration was observed in PCR product of chicken genomic DNA (right panel).

As also shown in FIG. 1, RFLP analysis confirmed the presence of the WHAM mutation in genomic DNA. Genomic DNA from normal and mutant homozygous male and hemizygous female chickens was amplified using PCR primers forward:

5'-GTCACTTCCCAAACAAAGCTA-3' SEQ ID No:9 reverse:

5'-ATGGACGCATTGAAGTTTCC-3' SEQ ID No:10 flanking the WHAM mutation, then the PCR products digested with HinfI. The WHAM alteration destroys a HinfI site, resulting in a 142 bp uncut fragment rather than the 106 bp and 36 bp fragments of normal chickens. The chicken sex chromosomes of each bird tested are indicated below the photo; male chickens are ZZ, female chickens are ZW.

The glutamate residue at the position of the non conservative E89K substitution is conserved between human (CAA10005), mouse (CAA53530), Takifugu rubripes ('fugu'), and chicken. The WHAM mutation is thus predicted to have a deleterious effect on activity of the ABC1 protein. The fugu amino acid sequence was predicted from nucleotide sequence of a cosmid containing the fugu ABC1 gene. Bitgood J J. 1985, "Additional linkage relationships within the Z chromosome of the chicken," *Poultry Science* 64: 2234–8 Bitgood J J. 1988, "Linear relationship of the loci for barring, dermal melanin inhibitor, and recessive white skin on the chicken Z chromosome," *Poultry Sci.* 67: 530–3.

Dietary Cholesterol and WHAM Chickens

Figure 2:
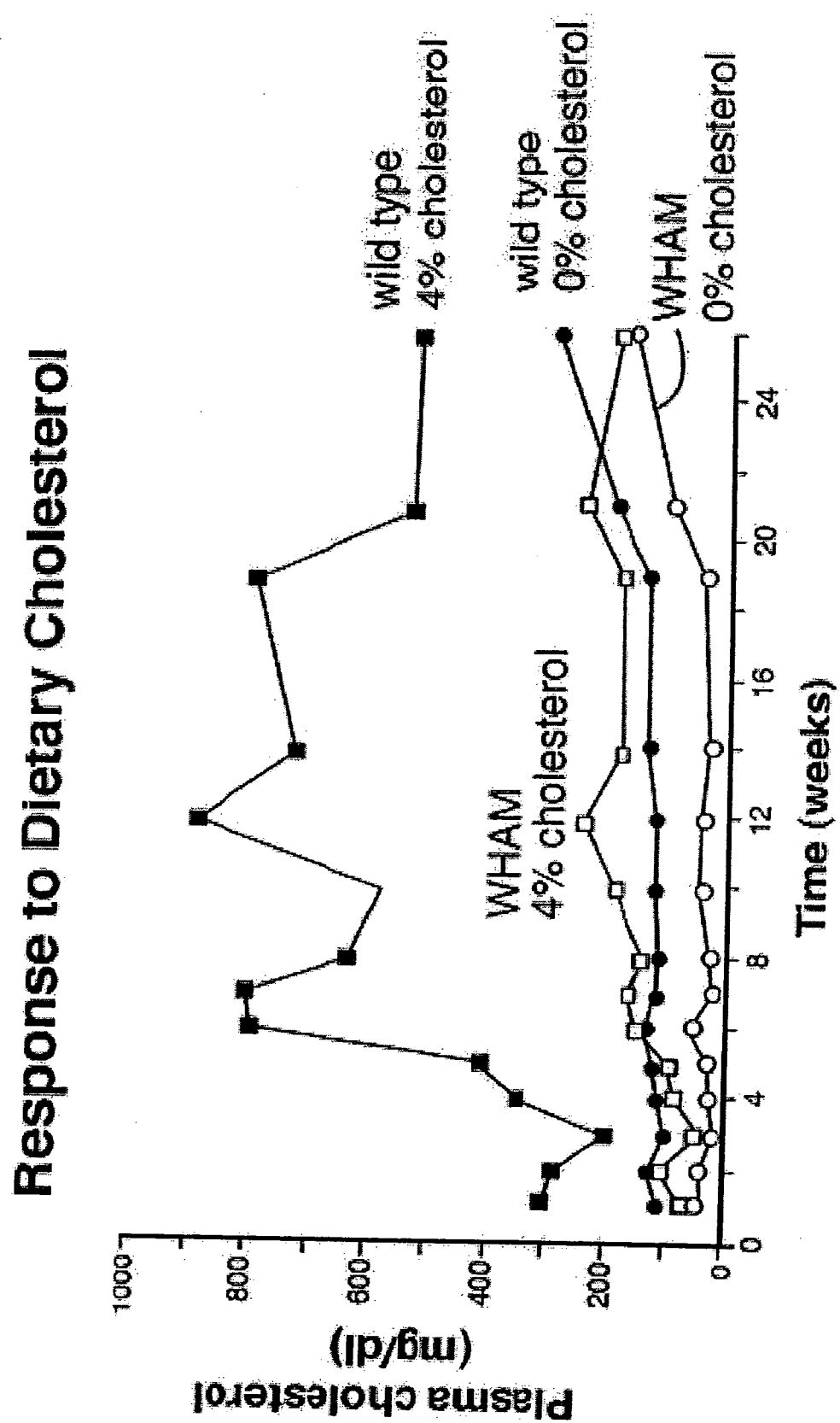
FIG. 2 is a graphical representation of some of the data from an example below.

FIG. 2 illustrates the results of time courses of plasma cholesterol in control and WHAM chickens on a cholesterol-free or high-cholesterol diet. The basal diet (ad libitum) was acorn-soy-based diet to which 12.4% (by weight) lard was added. By calculation, the diet contained 14% fat by weight or 37% as total calories. The two dietary treatments consisted of the basal (cholesterol-free) diet and the basal plus 4% cholesterol diet. The diets were each fed to two groups of chickes, each group comprising 10 animals, for 28 weeks.

This example demonstrates the effect of inhibition of ABC1 (here demonstrated by an inactivating mutation in the gene, but also obtainable by inhibitors of ABC1 identified by the screening assays of the invention) on cholesterol absorption by the WHAM chicken. Cholesterol transport from the lumen of the gut to the blood or lymph is blocked or eliminated by inhibition of the ABC1 gene. In this case the genetic mutation is a surrogate for an antagonist of the ABC1 protein.

Cholesterol Retention

Figure 3:
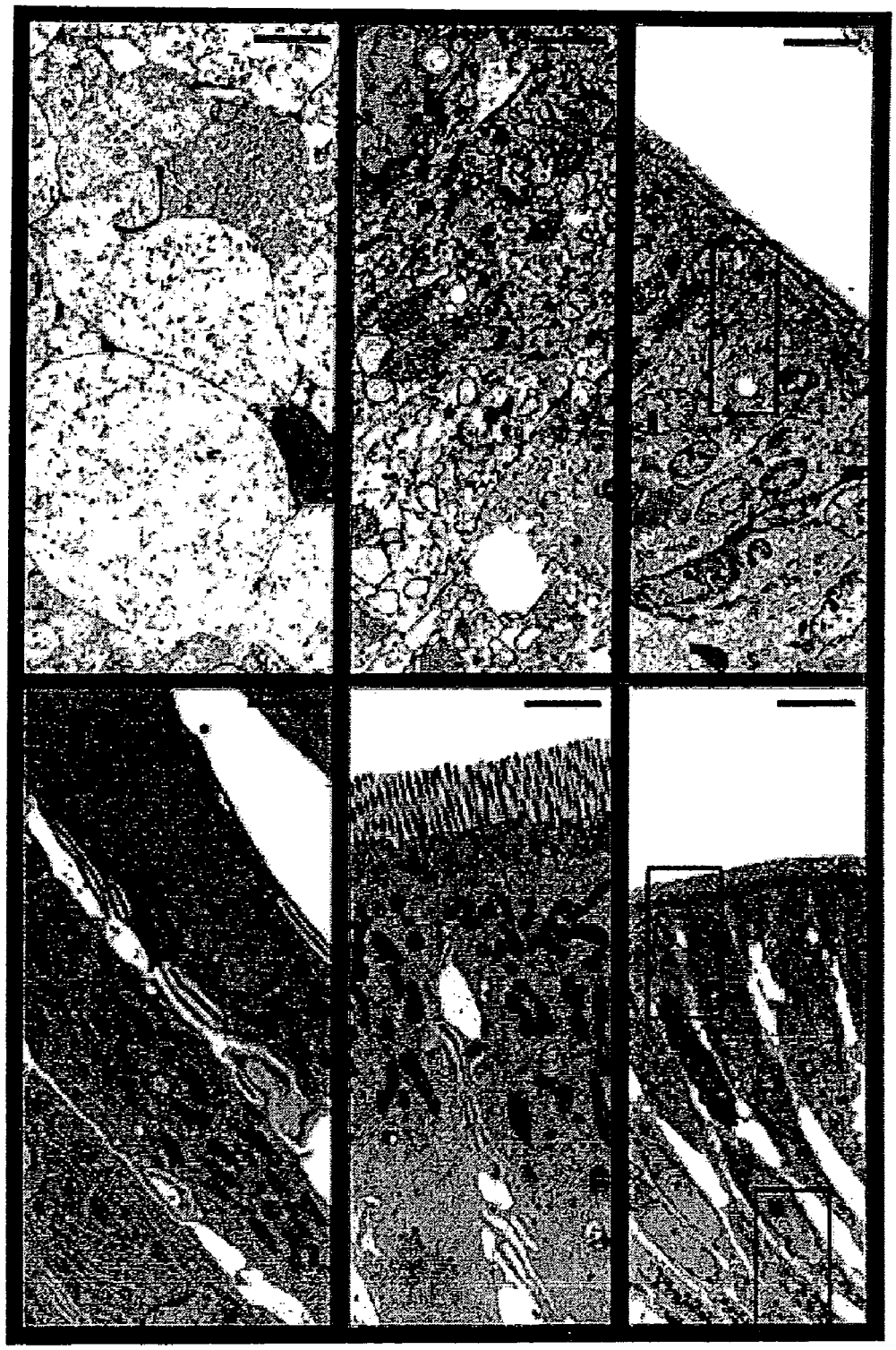
FIG. 3 is an electro-micrograph of the intestinal wall demonstrating accumulation of giant lipid droplets in WHAM chickens but not control chickens. The lipids are not found in columnar epithelial cells, but in deeper underlying cells of the lamina propria.

The WHAM chickens, like Tangier patients, show evidence of cholesterol ester retention. Like Tangier patients, the WHAM chickens have large non-osmiophilic drops in the cytoplasm of splenic macrophages. In addition, electromicrographs of the intestinal wall of the chicken (control and WHAM), show very specific accumulation of cholesterol in non-endothelial cells of the lamina propria. See FIG. 3 which shows those cells. In FIG. 3, cells of the intestinal wall, which are not columnar epithelium cells, from the WHAM chickens contain giant lipid droplets. In FIG. 3, photograph (A) shows normal intestine showing the microvilli at the apical surface. Spaces represent normal sites where chylomicron particles are secreted. Image (B) shows higher magnification of area shown in lower rectangle in (A). Image (C) is a higher magnification of intestinal wall from upper rectangle in (A). Photograph (D) shows the WHAM intestine showing apical surface, the absence of spaces between the cells, and accumulation of vesicles. Image (E) is a higher magnification of area in rectangle in (A). Note the abundance of vesicles relative to the control section in (B). Image (F) is a higher magnification of intestinal wall area just above the top of (D). Lipid inclusions 1.5–2.0 μm in diameter. Bar=2.5 μm in (A) and (D) and 0.6 μm in all other panels.

We conclude from this evidence that the WHAM chickens are able to absorb cholesterol from the intestinal lumen but are unable to transport that cholesterol out of the epithelial cells into the blood stream. This explains the accumulation of cholesterol in those cells.

Sulfonylurea Compounds

A drawback in the use of some sulfonylurea compounds is that such compounds can have unwanted activity in stimulating insulin secretion. Therefore, it is contemplated that a screening program be conducted to identify and assess either sulfonylurea or other compounds which have activity in inhibiting ABC1 but which do not stimulate unwanted insulin production. It is envisioned that this screen can be done by giving the compound orally to test animals. A tracer of radioactively labeled cholesterol can then be given to the animals. At various time points after administration (1, 2, 3, 4, 6, 8, 12, 16, 24, 36, and 48 hours), blood samples would be taken and the amount of the isotope in cholesterol and cholesterol ester of chylomicron particles would be sampled. The chylomicron fraction would be obtained by centrifuging the plasma in an ultracentrifuge (20,000 rpm in a 40.3 rotor for 20 minutes). The chylomicrons float to the top and are removed by aspiration. The area under the isotope amount versus time curve would then indicate the amount of tracer that has entered into the bloodstream. When divided by the amount initially administered in an oral dose, the percent of cholesterol that traveled from the intestinal lumen all the way into the bloodstream can be computed. Inhibitors of the function of the ABC1 protein or gene activity will reduce this amount. In in vivo assays, effects on insulin secretion can be measured by standard blood assays known in the art, such as a quantitative insulin radio-immunoassay.

In vitro screening assays for identifying unwanted activity in stimulating insulin secretion are also standard and known in the art. In a typical assay, islet cells are isolated from the pancreas by a collagenase digest. Cells are cultured; then exposed to the candidate substance. Insulin secretion by the cultured cells is measured by a quantitative radio-immunoassay. Candidate compounds which increase the level of insulin secretion are rejected as having undesirable side effects for the desired uses of the invention herein.

Inhibiting ABC1 Activity

Figure 4:
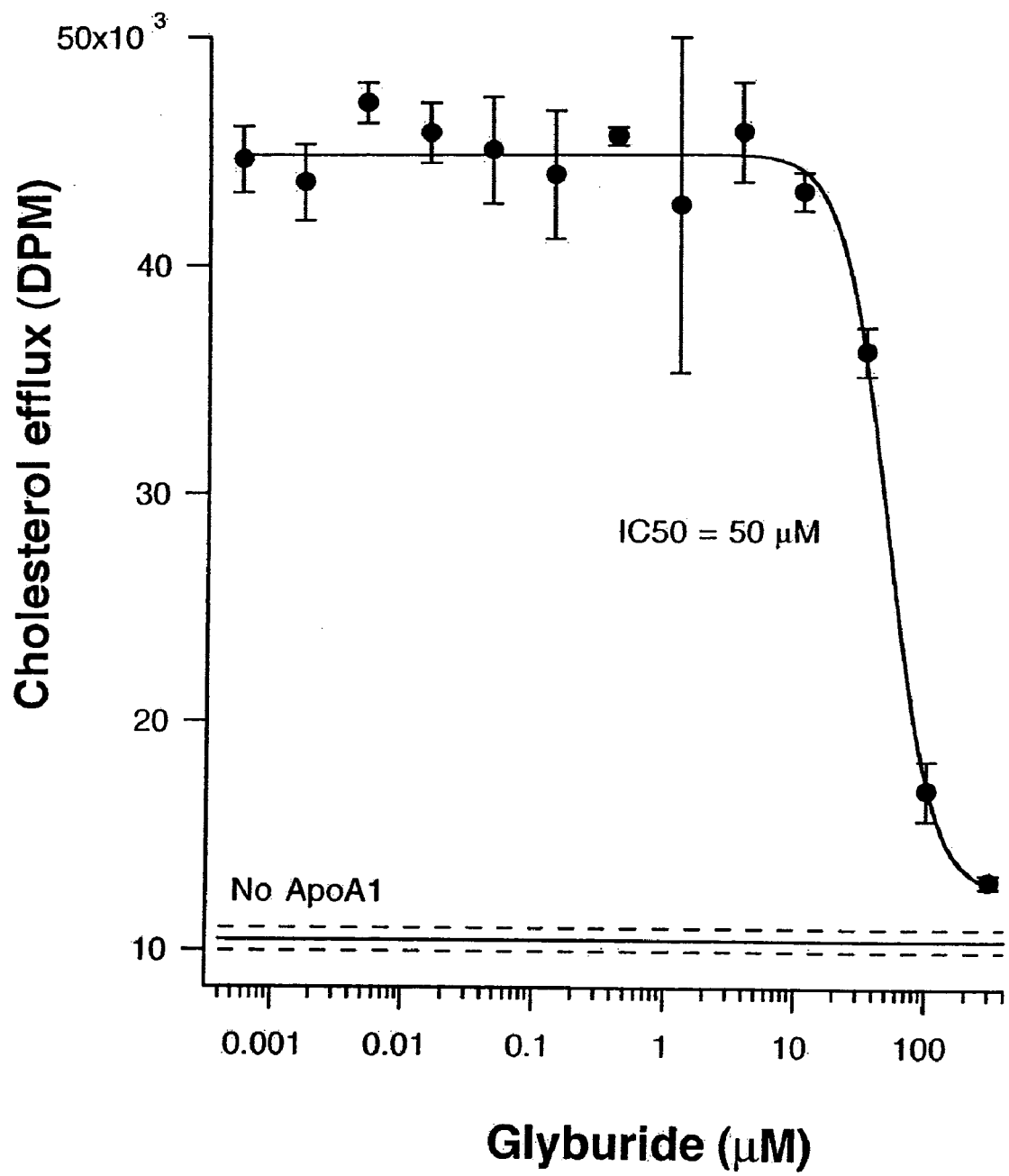
FIG. 4 is a graphical representation of data which demonstrates the response to dietary cholesterol in normal and WHAM chickens

ABC1 activity can be inhibited genetically or chemically. It is known that sulfonylurea drugs inhibit ABC1 activity. Shown in FIG. 4 is the results of a study demonstrating that effect. Mouse macrophages (J774) were labeled with $^3$H-cholesterol (2 μCi/ml) for 24 hours in 1% v/v fetal bovine serum. Following the labeling, the cells were equilibrated with 0.2% de-fatted bovine serum albumin in RPMI growth medium. Cholesterol efflux was initiated with the addition of 20 μg/ml of human apolipoprotein-A1 in the presence of the indicated concentrations of Glyburide, a sulfonylurea compound. After 24 hours, the medium was collected, centrifuged, and an aliquot collected for radioactivity determination by liquid scintillation counting.

This study demonstrates that the efficacy of a compound in inhibiting ABC1 activity can be measured in a cellular assay. This same assay can be used to test other compounds for ABC1 inhibitory activity.

The preceding examples and specification are illustrations of the invention which are non-limiting examples of the invention more generally described by the claims below.

The invention claimed is:

1. A method for inhibiting cholesterol uptake in the gut comprising the step of administering to an individual into the intestinal lumen an inhibitor of an ABC1 protein so as to selectively inhibit ABC 1 activity in the intestines to inhibit the transport of cholesterol from the intestinal lumen into the bloodstream, wherein the inhibitor is a sulfonylurea compound.

2. A method as claimed in claim 1 wherein the agent is administered orally.

3. A method for reducing transport of cholesterol from the gut to the blood comprising orally administering an ABC1 modulating compound to the intestinal lumen of an animal and thereby reducing such transport so as to selectively inhibit ABC 1 activity in the intestine to inhibit the transport of cholesterol from the intestinal lumen into the bloodstream, wherein the compound is a sulfonylurea compound.

4. A method for reducing transport of cholesterol from the gut to the blood comprising administering glyburide to the intestinal lumen of an animal and thereby reducing such transport so as to selectively inhibit ABC 1 activity in the intestine to inhibit the transport of cholesterol from the intestinal lumen into the bloodstream.

* * * * *

UNITED STATES PATENT AND TRADEMARK OFFICE
CERTIFICATE OF CORRECTION

| | | |
|---|---|---|
| PATENT NO. | : 7,166,584 B1 | Page 1 of 1 |
| APPLICATION NO. | : 09/704272 | |
| DATED | : January 23, 2007 | |
| INVENTOR(S) | : Alan D. Attie et al. | |

It is certified that error appears in the above-identified patent and that said Letters Patent is hereby corrected as shown below:

Column 1,
    Please insert at line 5 the following:

--STATEMENT REGARDING FEDERALLY SPONSORED RESEARCH OR DEVELOPMENT

This invention was made with United States government support awarded by the following agency:

NIH Grant RO1 HL56593-02

The United States has certain rights in this invention.--

Signed and Sealed this

Seventeenth Day of April, 2007

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 7862
<212> TYPE: DNA
<213> ORGANISM: Homo sapiens

<400> SEQUENCE: 1
gtccctgctg tgagctctgg ccgctgcctt ccagggctcc cgagccacac gctgggggtg      60
ctggctgagg gaacatggct tgttggcctc agctgaggtt gctgctgtgg aagaacctca     120
ctttcagaag aagacaaaca tgtcagctgc tgctggaagt ggcctggcct ctatttatct     180
tcctgatcct gatctctgtt cggctgagct acccaccta tgaacaacat gaatgccatt     240
```

-continued

```
ttccaaataa agccatgccc tctgcaggaa cacttccttg ggttcagggg attatctgta      300
atgccaacaa cccctgtttc cgttacccga ctcctgggga ggctcccgga gttgttggaa      360
actttaacaa atccattgtg gctcgcctgt tctcagatgc tcggaggctt cttttataca      420
gccagaaaga caccagcatg aaggacatgc gcaaagttct gagaacatta cagcagatca      480
agaaatccag ctcaaacttg aagcttcaag atttcctggt ggacaatgaa accttctctg      540
ggttcctgta tcacaacctc tctctcccaa agtctactgt ggacaagatg ctgagggctg      600
atgtcattct ccacaaggta ttttttgcaag gctaccagtt acatttgaca agtctgtgca     660
atggatcaaa atcagaagag atgattcaac ttggtgacca agaagtttct gagctttgtg      720
gcctaccaag ggagaaactg gctgcagcag agcgagtact tcgttccaac atggacatcc      780
tgaagccaat cctgagaaca ctaaactcta catctcccct cccgagcaag gagctggctg      840
aagccacaaa aacattgctg catagtcttg ggactctggc ccaggagctg ttcagcatga      900
gaagctggag tgacatgcga caggaggtga tgtttctgac caatgtgaac agctccagct      960
cctccaccca aatctaccag gctgtgtctc gtattgtctg cgggcatccc gagggagggg     1020
ggctgaagat caagtctctc aactggtatg aggacaacaa ctacaaagcc ctctttggag     1080
gcaatggcac tgaggaagat gctgaaacct tctatgacaa ctctacaact ccttactgca     1140
atgatttgat gaagaatttg gagtctagtc ctctttcccg cattatctgg aaagctctga     1200
agccgctgct cgttgggaag atcctgtata cacctgacac tccagccaca aggcaggtca     1260
tggctgaggt gaacaagacc ttccaggaac tggctgtgtt ccatgatctg gaaggcatgt     1320
gggaggaact cagccccaag atctggacct tcatggagaa cagccaagaa atggaccttg     1380
tccggatgct gttggacagc agggacaatg accacttttg ggaacagcag ttggatggct     1440
tagattggac agcccaagac atcgtggcgt ttttggccaa gcacccagag gatgtccagt     1500
ccagtaatgg tttctgtgta cacctggaga gaagctttca acgagactaa ccaggcaatc     1560
cggaccatat ctcgcttcat ggagtgtgtc aacctgaaca agctagaacc catagcaaca     1620
gaagtctggc tcatcaacaa gtccatggag ctgctggatg agaggaagtt ctgggctggt     1680
attgtgttca ctggaattac tccaggcagc attgagctgc cccatcatgt caagtacaag     1740
atccgaatgg acattgacaa tgtggagagg acaaataaaa tcaaggatgg gtactgggac     1800
cctggtcctc gagctgaccc cttttgaggac atgcggtacg tctgggggg cttcgcctac     1860
ttgcaggatg tggtggagca ggcaatcatc agggtgctga cgggcaccga aagaaaact     1920
ggtgtctata tgcaacagat gccctatccc tgttacgttg atgacatctt tctgcgggtg     1980
atgagccggt caatgcccct cttcatgacg ctggcctgga tttactcagt ggctgtgatc     2040
atcaagggca tcgtgtatga aaggaggca cggctgaaag agaccatgcg gatcatgggc     2100
ctggacaaca gcatcctctg gtttagctgg ttcattagta gcctcattcc tcttcttgtg     2160
agcgctggcc tgctagtggt catcctgaag ttaggaaacc tgctgcccta cagtgatccc     2220
agcgtggtgt ttgtcttcct gtccgtgttt gctgtggtga caatcctgca gtgcttcctg     2280
attagcacac tcttctccag agccaacctg gcagcagcct gtgggggggca tcatctactt     2340
cacgctgtac ctgccctacg tcctgtgtgt ggcatggcag gactacgtgg gcttcacact     2400
caagatcttc gctagcctgc tgtctcctgt ggcttttggg tttggctgtg agtactttgc     2460
cctttttgag gagcagggca ttggagtgca gtgggacaac ctgtttgaga gtcctgtgga     2520
ggaagatggc ttcaatctca ccacttcggt ctccatgatg ctgtttgaca ccttcctcta     2580
tggggtgatg acctggtaca ttgaggctgt cttttccaggc cagtacggaa ttcccaggcc     2640
```

-continued

```
ctggtatttt ccttgcacca agtcctactg gtttggcgag gaaagtgatg agaagagcca    2700
ccctggttcc aaccagaaga gaatatcaga atctgcatg gaggaggaac ccacccactt    2760
gaagctgggc gtgtccattc agaacctggt aaaagtctac cgagatggga tgaaggtggc    2820
tgtcgatggc ctggcactga atttttatga gggccagatc acctccttcc tgggccacaa    2880
tggagcgggg aagacgacca ccatgtcaat cctgaccggg ttgttccccc cgacctcggg    2940
caccgcctac atcctgggaa aagacattcg ctctgagatg agcaccatcc ggcagaacct    3000
gggggtctgt ccccagcata acgtgctgtt tgacatgctg actgtcgaag aacacatctg    3060
gttctatgcc cgcttgaaag ggctctctga gaagcacgtg aaggcggaga tggagcagat    3120
ggccctggat gttggtttgc catcaagcaa gctgaaaagc aaaacaagcc agctgtcagg    3180
tggaatgcag agaaagctat ctgtggcctt ggcctttgtc ggggatcta aggttgtcat    3240 tctggatgaa cccacagctg gtgtggaccc ttactcccgc aggggaatat gggagctgct    3300
gctgaaatac cgacaaggcc gcaccattat tctctctaca caccacatgg atgaagcgga    3360
cgtcctgggg gacaggattg ccatcatctc ccatgggaag ctgtgctgtg tgggctcctc    3420
cctgtttctg aagaaccagc tgggaacagg ctactacctg accttggtca agaaagatgt    3480
ggaatcctcc ctcagttcct gcagaaacag tagtagcact gtgtcatacc tgaaaaagga    3540
ggacagtgtt tctcagagca gttctgatgc tggcctgggc agcgaccatg agagtgacac    3600
gctgaccatc gatgtctctg ctatctccaa cctcatcagg aagcatgtgt ctgaagcccg    3660
gctggtggaa gacataggc atgagctgac ctatgtgctg ccatatgaag ctgctaagga    3720
gggagccttt gtggaactct ttcatgagat tgatgaccgg ctctcagacc tgggcatttc    3780
tagttatggc atctcagaga cgaccctgga agaaatattc ctcaaggtgg ccgaagagag    3840
tggggtggat gctgagacct cagatggtac cttgccagca agacgaaaca ggcgggcctt    3900
cggggacaag cagagctgtc ttcgcccgtt cactgaagat gatgctgctg atccaaatga    3960
ttctgacata gacccagaat ccagagagac agacttgctc agtgggatgg atggcaaagg    4020
gtcctaccag gtgaaaggct ggaaacttac acagcaacag tttgtggccc ttttgtggaa    4080
gagactgcta attgccagac ggagtcggaa aggattttt gctcagattg tcttgccagc    4140
tgtgtttgtc tgcattgccc ttgtgttcag cctgatcgtg ccacccttg gcaagtaccc    4200 cagcctggaa cttcagccct ggatgtacaa cgaacagtac acatttgtca gcaatgatgc    4260
tcctgaggac acgggaaccc tggaactctt aaacgccctc accaaagacc ctggcttcgg    4320
gacccgctgt atgaaggaa acccaatccc agacacgccc tgccaggcag gggaggaaga    4380
gtggaccact gccccagttc cccagaccat catggaccct ttccgaatg ggaactggac    4440 aatgcagaac ccttcacctg catgccagtg tagcagcgac aaaatcaaga agatgctgcc    4500
tgtgtgtccc ccagggggcag ggggggctgcc tcctccacaa agaaaacaaa acactgcaga    4560
tatccttcag gacctgacag gaagaaacat ttcggattat ctggtgaaga cgtatgtgca    4620
gatcatagcc aaaagcttaa agaacaagat ctgggtgaat gagtttaggt atggcggctt    4680
ttccctgggt gtcagtaata tccaagcact tcctccgagt caagaagtta atgatgccat    4740
caaacaaatg aagaaacacc taaagctggc caaggacagt tctgcagatc gatttctcaa    4800
cagcttggga agatttatga caggactgga caccagaaat aatgtcaagg tgtggttcaa    4860
taacaagggc tggcatgcaa tcagctcttt cctgaatgtc atcaacaatg ccattctccg    4920
ggccaacctg caaaagggag agaaccctag ccattatgga attactgctt tcaatcatcc    4980
```

```
cctgaatctc accaagcagc agctctcaga ggtggctctg atgaccacat cagtggatgt   5040
ccttgtgtcc atctgtgtca tctttgcaat gtccttcgtc ccagccagct tgtcgtatt   5100 cctgatccag gagcgggtca gcaaagcaaa acacctgcag ttcatcagtg gagtgaagcc   5160
tgtcatctac tggctctcta attttgtctg ggatatgtgc aattacgttg tccctgccac   5220
actggtcatt atcatcttca tctgcttcca gcagaagtcc tatgtgtcct ccaccaatct   5280
gcctgtgcta gcccttctac ttttgctgta tgggtggtca atcacacctc tcatgtaccc   5340
agcctccttt gtgttcaaga tccccagcac agcctatgtg gtgctcacca gcgtgaacct   5400
cttcattggc attaatggca gcgtggccac ctttgtgctg gagctgttca ccgacaataa   5460
gctgaataat atcaatgata tcctgaagtc cgtgttcttg atcttccac attttttgcct   5520 gggacgaggg ctcatcgaca tggtgaaaaa ccaggcaatg gctgatgccc tggaaaggtt   5580
tggggagaat cgctttgtgt caccattatc ttgggacttg gtgggacgaa acctcttcgc   5640 catgccgtg gaaggggtgg tgttcttcct cattactgtt ctgatccagt acagattctt   5700
catcaggccc agacctgtaa atgcaaagct atctcctctg aatgatgaag atgaagatgt   5760
gaggcgggaa agacagagaa ttcttgatgg tggaggccag aatgacatct tagaaatcaa   5820
ggagttgacg aagatatata aaggaagcg gaagcctgct gttgacagga tttgcgtggg   5880
cattcctcct ggtgagtgct ttgggctcct gggagttaat ggggctggaa atcatcaac   5940 tttcaagatg ttaacaggag ataccactgt taccagagga gatgctttcc ttaacaaaaa   6000
tagtatctta tcaaacatcc atgaagtaca tcagaacatg ggctactgcc ctcagtttga   6060
tgccatcaca gagctgttga ctgggagaga acacgtggag ttcttttgccc ttttgagagg   6120 agtcccagag aaagaagttg gcaaggttgg tgagtgggcg attcggaaac tgggcctcgt   6180
gaagtatgga gaaaaatatg ctggtaacta tagtggaggc aacaaacgca agctctctac   6240
agccatggct ttgatcggcg ggcctcctgt ggtgtttctg gatgaaccca ccacaggcat   6300
ggatcccaaa gcccggcggt tcttgtggaa ttgtgcccta agtgttgtca aggaggggag   6360
atcagtagtg cttacatctc atagtatgga agaatgtgaa gctctttgca ctaggatggc   6420
aatcatggtc aatggaaggt tcaggtgcct tggcagtgtc cagcatctaa aaaataggtt   6480
tggagatggt tatacaatag ttgtacgaat agcagggtcc aacccggacc tgaagcctgt   6540
ccaggatttc tttggacttg catttcctgg aagtgttcta aaagagaaac accggaacat   6600
gctacaatac cagcttccat cttcattatc ttctctggcc aggatattca gcatcctctc   6660
ccagagcaaa aagcgactcc acatagaaga ctactctgtt tctcagacaa cacttgacca   6720
agtatttgtg aactttgcca aggaccaaag tgatgatgac cacttaaaag acctctcatt   6780
acacaaaaac cagacagtag tggacgttgc agttctcaca tcttttctac aggatgagaa   6840
agtgaaagaa agctatgtat gaagaatcct gttcatacgg ggtggctgaa agtaaagagg   6900
aactagactt tccttttgcac catgtgaagt gttgtggaga aaagagccag aagttgatgt   6960
gggaagaagt aaactggata ctgtactgat actattcaat gcaatgcaat tcaatgcaat   7020
gaaaacaaaa ttccattaca ggggcagtgc ctttgtagcc tatgtcttgt atggctctca   7080
agtgaaagac ttgaatttag ttttttacct ataccttatgt gaaactctat tatggaaccc   7140 aatgacata tgggtttgaa ctcacacttt tttttttttt tttgttcctg tgtattctca   7200
ttggggttgc aacaataatt catcaagtaa tcatggccag cgattattga tcaaaatcaa   7260
aaggtaatgc acatcctcat tcactaagcc atgccatgcc caggagactg gtttcccggt   7320
gacacatcca ttgctggcaa tgagtgtgcc agagttatta gtgccaagtt tttcagaaag   7380
```

-continued

```
tttgaagcac catggtgtgt catgctcact tttgtgaaag ctgctctgct cagagtctat    7440
caacattgaa tatcagttga cagaatggtg ccatgcgtgg ctaacatcct gctttgattc    7500
cctctgataa gctgttctgg tggcagtaac atgcaacaaa aatgtgggtg tctccaggca    7560
cgggaaactt ggttccattg ttatattgtc ctatgcttcg agccatgggt ctacagggtc    7620
atccttatga gactcttaaa tatacttaga tcctggtaag aggcaaagaa tcaacagcca    7680
aactgctggg gctgcaactg ctgaagccag ggcatgggat taaagagatt gtgcgttcaa    7740
acctagggaa gcctgtgccc atttgtcctg actgtctgct aacatggtac actgcatctc    7800
aagatgttta tctgacacaa gtgtattatt tctggctttt tgaattaatc tagaaaatga    7860
aa                                                                  7862
```

<210> SEQ ID NO 2
<211> LENGTH: 2258
<212> TYPE: PRT
<213> ORGANISM: Homo sapiens

<400> SEQUENCE: 2

```
Met Ala Cys Trp Pro Gln Leu Arg Leu Leu Trp Lys Asn Leu Thr
  1               5                  10                  15

Phe Arg Arg Arg Gln Thr Cys Gln Leu Leu Glu Val Ala Trp Pro
                 20                  25                  30

Leu Phe Ile Phe Leu Ile Leu Ile Ser Val Arg Leu Ser Tyr Pro Pro
             35                  40                  45

Tyr Glu Gln His Glu Cys His Phe Pro Asn Lys Ala Met Pro Ser Ala
         50                  55                  60

Gly Thr Leu Pro Trp Val Gln Gly Ile Ile Cys Asn Ala Asn Asn Pro
 65                  70                  75                  80

Cys Phe Arg Tyr Pro Thr Pro Gly Glu Ala Pro Gly Val Val Gly Asn
                 85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
            115                 120                 125

Leu Arg Thr Leu Gln Gln Ile Lys Lys Ser Ser Asn Leu Lys Leu
            130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
            195                 200                 205

Gln Glu Val Ser Glu Leu Cys Gly Leu Pro Arg Glu Lys Leu Ala Ala
            210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
            260                 265                 270

Phe Ser Met Arg Ser Trp Ser Asp Met Arg Gln Glu Val Met Phe Leu
```

-continued

```
              275                 280                 285
Thr Asn Val Asn Ser Ser Ser Ser Thr Gln Ile Tyr Gln Ala Val
290                 295                 300
Ser Arg Ile Val Cys Gly His Pro Glu Gly Gly Leu Lys Ile Lys
305                 310                 315                 320
Ser Leu Asn Trp Tyr Glu Asp Asn Asn Tyr Lys Ala Leu Phe Gly Gly
                325                 330                 335
Asn Gly Thr Glu Glu Asp Ala Glu Thr Phe Tyr Asp Asn Ser Thr Thr
                340                 345                 350
Pro Tyr Cys Asn Asp Leu Met Lys Asn Leu Glu Ser Ser Pro Leu Ser
            355                 360                 365
Arg Ile Ile Trp Lys Ala Leu Lys Pro Leu Leu Val Gly Lys Ile Leu
        370                 375                 380
Tyr Thr Pro Asp Thr Pro Ala Thr Arg Gln Val Met Ala Glu Val Asn
385                 390                 395                 400
Lys Thr Phe Gln Glu Leu Ala Val Phe His Asp Leu Glu Gly Met Trp
                405                 410                 415
Glu Glu Leu Ser Pro Lys Ile Trp Thr Phe Met Glu Asn Ser Gln Glu
            420                 425                 430
Met Asp Leu Val Arg Met Leu Leu Asp Ser Arg Asp Asn Asp His Phe
        435                 440                 445
Trp Glu Gln Gln Leu Asp Gly Leu Asp Trp Thr Ala Gln Asp Ile Val
    450                 455                 460
Ala Phe Leu Ala Lys His Pro Glu Asp Val Gln Ser Ser Asn Gly Ser
465                 470                 475                 480
Val Tyr Thr Trp Arg Glu Ala Phe Asn Glu Thr Asn Gln Ala Ile Arg
                485                 490                 495
Thr Ile Ser Arg Phe Met Glu Cys Val Asn Leu Asn Lys Leu Glu Pro
            500                 505                 510
Ile Ala Thr Glu Val Trp Leu Ile Asn Lys Ser Met Glu Leu Leu Asp
        515                 520                 525
Glu Arg Lys Phe Trp Ala Gly Ile Val Phe Thr Gly Ile Thr Pro Gly
    530                 535                 540
Ser Ile Glu Leu Pro His His Val Lys Tyr Lys Ile Arg Met Asp Ile
545                 550                 555                 560
Asp Asn Val Glu Arg Thr Asn Lys Ile Lys Asp Gly Tyr Trp Asp Pro
                565                 570                 575
Gly Pro Arg Ala Asp Pro Phe Glu Asp Met Arg Tyr Val Trp Gly Gly
            580                 585                 590
Phe Ala Tyr Leu Gln Asp Val Val Glu Gln Ala Ile Ile Arg Val Leu
        595                 600                 605
Thr Gly Thr Glu Lys Lys Thr Gly Val Tyr Met Gln Gln Met Pro Tyr
    610                 615                 620
Pro Cys Tyr Val Asp Asp Ile Phe Leu Arg Val Met Ser Arg Ser Met
625                 630                 635                 640
Pro Leu Phe Met Thr Leu Ala Trp Ile Tyr Ser Val Ala Val Ile Ile
                645                 650                 655
Lys Gly Ile Val Tyr Glu Lys Glu Ala Arg Leu Lys Glu Thr Met Arg
            660                 665                 670
Ile Met Gly Leu Asp Asn Ser Ile Leu Trp Phe Ser Trp Phe Ile Ser
        675                 680                 685
Ser Leu Ile Pro Leu Leu Val Ser Ala Gly Leu Leu Val Val Ile Leu
    690                 695                 700
```

-continued

```
Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Ala Trp Gln Asp Tyr Val
        755                 760                 765

Gly Phe Thr Leu Lys Ile Phe Ala Ser Leu Leu Ser Pro Val Ala Phe
    770                 775                 780

Gly Phe Gly Cys Glu Tyr Phe Ala Leu Phe Glu Gln Gly Ile Gly
785                 790                 795                 800

Val Gln Trp Asp Asn Leu Phe Glu Ser Pro Val Glu Glu Asp Gly Phe
                805                 810                 815

Asn Leu Thr Thr Ser Val Ser Met Met Leu Phe Asp Thr Phe Leu Tyr
                820                 825                 830

Gly Val Met Thr Trp Tyr Ile Glu Ala Val Phe Pro Gly Gln Tyr Gly
            835                 840                 845

Ile Pro Arg Pro Trp Tyr Phe Pro Cys Thr Lys Ser Tyr Trp Phe Gly
850                 855                 860

Glu Glu Ser Asp Glu Lys Ser His Pro Gly Ser Asn Gln Lys Arg Ile
865                 870                 875                 880

Ser Glu Ile Cys Met Glu Glu Pro Thr His Leu Lys Leu Gly Val
                885                 890                 895

Ser Ile Gln Asn Leu Val Lys Val Tyr Arg Asp Gly Met Lys Val Ala
            900                 905                 910

Val Asp Gly Leu Ala Leu Asn Phe Tyr Glu Gly Gln Ile Thr Ser Phe
        915                 920                 925

Leu Gly His Asn Gly Ala Gly Lys Thr Thr Thr Met Ser Ile Leu Thr
    930                 935                 940

Gly Leu Phe Pro Pro Thr Ser Gly Thr Ala Tyr Ile Leu Gly Lys Asp
945                 950                 955                 960

Ile Arg Ser Glu Met Ser Thr Ile Arg Gln Asn Leu Gly Val Cys Pro
                965                 970                 975

Gln His Asn Val Leu Phe Asp Met Leu Thr Val Glu Glu His Ile Trp
                980                 985                 990

Phe Tyr Ala Arg Leu Lys Gly Leu Ser Glu Lys His Val Lys Ala Glu
            995                 1000                1005

Met Glu Gln Met Ala Leu Asp Val Gly Leu Pro Ser Ser Lys Leu Lys
    1010                1015                1020

Ser Lys Thr Ser Gln Leu Ser Gly Gly Met Gln Arg Lys Leu Ser Val
1025                1030                1035                1040

Ala Leu Ala Phe Val Gly Gly Ser Lys Val Val Ile Leu Asp Glu Pro
                1045                1050                1055

Thr Ala Gly Val Asp Pro Tyr Ser Arg Arg Gly Ile Trp Glu Leu Leu
                1060                1065                1070

Leu Lys Tyr Arg Gln Gly Arg Thr Ile Ile Leu Ser Thr His His Met
        1075                1080                1085

Asp Glu Ala Asp Val Leu Gly Asp Arg Ile Ala Ile Ile Ser His Gly
    1090                1095                1100

Lys Leu Cys Cys Val Gly Ser Ser Leu Phe Leu Lys Asn Gln Leu Gly
1105                1110                1115                1120
```

-continued

```
Thr Gly Thr Thr Leu Thr Leu Val Lys Lys Asp Val Glu Ser Ser Leu
            1125                1130                1135

Ser Ser Cys Arg Asn Ser Ser Ser Thr Val Ser Tyr Leu Lys Lys Glu
            1140                1145                1150

Asp Ser Val Ser Gln Ser Ser Asp Ala Gly Leu Gly Ser Asp His
            1155                1160                1165

Glu Ser Asp Thr Leu Thr Ile Asp Val Ser Ala Ile Ser Asn Leu Ile
            1170                1175                1180

Arg Lys His Val Ser Glu Ala Arg Leu Val Glu Asp Ile Gly His Glu
1185                1190                1195                1200

Leu Thr Tyr Val Leu Pro Tyr Glu Ala Ala Lys Glu Gly Ala Phe Val
            1205                1210                1215

Glu Leu Phe His Glu Ile Asp Asp Arg Leu Ser Asp Leu Gly Ile Ser
            1220                1225                1230

Ser Tyr Gly Ile Ser Glu Thr Thr Leu Glu Glu Ile Phe Leu Lys Val
            1235                1240                1245

Ala Glu Glu Ser Gly Val Asp Ala Glu Thr Ser Asp Gly Thr Leu Pro
            1250                1255                1260

Ala Arg Arg Asn Arg Arg Ala Phe Gly Asp Lys Gln Ser Cys Leu Arg
1265                1270                1275                1280

Pro Phe Thr Glu Asp Asp Ala Ala Asp Pro Asn Asp Ser Asp Ile Asp
            1285                1290                1295

Pro Glu Ser Arg Glu Thr Asp Leu Leu Ser Gly Met Asp Gly Lys Gly
            1300                1305                1310

Ser Tyr Gln Val Lys Gly Trp Lys Leu Thr Gln Gln Phe Val Ala
            1315                1320                1325

Leu Leu Trp Lys Arg Leu Leu Ile Ala Arg Arg Ser Arg Lys Gly Phe
            1330                1335                1340

Phe Ala Gln Ile Val Leu Pro Ala Val Phe Val Cys Ile Ala Leu Val
1345                1350                1355                1360

Phe Ser Leu Ile Val Pro Pro Phe Gly Lys Tyr Pro Ser Leu Glu Leu
            1365                1370                1375

Gln Pro Trp Met Tyr Asn Glu Gln Tyr Thr Phe Val Ser Asn Asp Ala
            1380                1385                1390

Pro Glu Asp Thr Gly Thr Leu Glu Leu Leu Asn Ala Leu Thr Lys Asp
            1395                1400                1405

Pro Gly Phe Gly Thr Arg Cys Met Glu Gly Asn Pro Ile Pro Asp Thr
            1410                1415                1420

Pro Cys Gln Ala Gly Glu Glu Glu Trp Thr Thr Ala Pro Val Pro Gln
1425                1430                1435                1440

Thr Ile Met Asp Leu Phe Gln Asn Gly Asn Trp Thr Met Gln Asn Pro
            1445                1450                1455

Ser Pro Ala Cys Gln Cys Ser Ser Asp Lys Ile Lys Lys Met Leu Pro
            1460                1465                1470

Val Cys Pro Pro Gly Ala Gly Gly Leu Pro Pro Gln Arg Lys Gln
            1475                1480                1485

Asn Thr Ala Asp Ile Leu Gln Asp Leu Thr Gly Arg Asn Ile Ser Asp
            1490                1495                1500

Tyr Leu Val Lys Thr Tyr Val Gln Ile Ile Ala Lys Ser Leu Lys Asn
1505                1510                1515                1520

Lys Ile Trp Val Asn Glu Phe Arg Tyr Gly Gly Phe Ser Leu Gly Val
            1525                1530                1535

Ser Asn Thr Trp Ala Leu Pro Pro Ser Gln Glu Val Asn Asp Ala Ile
```

-continued

```
            1540              1545              1550
Lys Gln Met Lys Lys His Leu Lys Leu Ala Lys Asp Ser Ser Ala Asp
         1555              1560              1565
Arg Phe Leu Asn Ser Leu Gly Arg Phe Met Thr Gly Leu Asp Thr Arg
    1570              1575              1580
Asn Asn Val Lys Val Trp Phe Asn Asn Lys Gly Trp His Ala Ile Ser
1585              1590              1595              1600
Ser Phe Leu Asn Val Ile Asn Asn Ala Ile Leu Arg Ala Asn Leu Gln
             1605              1610              1615
Lys Gly Glu Asn Pro Ser His Trp Gly Ile Thr Ala Phe Asn His Pro
         1620              1625              1630
Leu Asn Leu Thr Lys Gln Gln Leu Ser Glu Val Ala Leu Met Thr Thr
    1635              1640              1645
Ser Val Asp Val Leu Val Ser Ile Cys Val Ile Phe Ala Met Ser Phe
    1650              1655              1660
Val Pro Ala Ser Phe Val Val Phe Leu Ile Gln Glu Arg Val Ser Lys
1665              1670              1675              1680
Ala Lys His Leu Gln Phe Ile Ser Gly Val Lys Pro Val Ile Tyr Trp
             1685              1690              1695
Leu Ser Asn Phe Val Trp Asp Met Cys Asn Tyr Val Val Pro Ala Thr
         1700              1705              1710
Leu Val Ile Ile Ile Phe Ile Cys Phe Gln Gln Lys Ser Tyr Val Ser
         1715              1720              1725
Ser Thr Asn Leu Pro Val Leu Ala Leu Leu Leu Leu Tyr Gly Trp
         1730              1735              1740
Ser Ile Thr Pro Leu Met Tyr Pro Ala Ser Phe Val Phe Lys Ile Pro
1745              1750              1755              1760
Ser Thr Ala Tyr Val Val Leu Thr Ser Val Asn Leu Phe Ile Gly Ile
             1765              1770              1775
Asn Gly Ser Val Ala Thr Phe Val Leu Glu Leu Phe Thr Asp Asn Lys
         1780              1785              1790
Leu Asn Asn Ile Asn Asp Ile Leu Lys Ser Val Phe Leu Ile Phe Pro
    1795              1800              1805
His Phe Cys Leu Gly Arg Gly Leu Ile Asp Met Val Lys Asn Gln Ala
    1810              1815              1820
Met Ala Asp Ala Leu Glu Arg Phe Gly Glu Asn Arg Phe Val Ser Pro
1825              1830              1835              1840
Leu Ser Trp Asp Leu Val Gly Arg Asn Leu Phe Ala Met Ala Val Glu
             1845              1850              1855
Gly Val Val Phe Phe Leu Ile Thr Val Leu Ile Gln Tyr Arg Phe Phe
         1860              1865              1870
Ile Arg Pro Arg Pro Val Asn Ala Lys Leu Ser Pro Leu Asn Asp Glu
         1875              1880              1885
Asp Glu Asp Val Arg Arg Glu Arg Gln Arg Ile Leu Asp Gly Gly Gly
    1890              1895              1900
Gln Asn Asp Ile Leu Glu Ile Lys Glu Leu Thr Lys Ile Tyr Arg Arg
1905              1910              1915              1920
Lys Arg Lys Pro Ala Val Asp Arg Ile Cys Val Gly Ile Pro Pro Gly
             1925              1930              1935
Glu Cys Phe Gly Leu Leu Gly Val Asn Gly Ala Gly Lys Ser Ser Thr
         1940              1945              1950
Phe Lys Met Leu Thr Gly Asp Thr Val Thr Arg Gly Asp Ala Phe
         1955              1960              1965
```

-continued

```
Leu Asn Lys Asn Ser Ile Leu Ser Asn Ile His Glu Val His Gln Asn
    1970                1975                1980
Met Gly Tyr Cys Pro Gln Phe Asp Ala Ile Thr Glu Leu Leu Thr Gly
1985                1990                1995                2000
Arg Glu His Val Glu Phe Phe Ala Leu Leu Arg Gly Val Pro Glu Lys
                2005                2010                2015
Glu Val Gly Lys Val Gly Glu Trp Ala Ile Arg Lys Leu Gly Leu Val
                2020                2025                2030
Lys Tyr Gly Glu Lys Tyr Ala Gly Asn Tyr Ser Gly Gly Asn Lys Arg
            2035                2040                2045
Lys Leu Ser Thr Ala Met Ala Leu Ile Gly Gly Pro Pro Val Val Phe
    2050                2055                2060
Leu Asp Glu Pro Thr Thr Gly Met Asp Pro Lys Ala Arg Arg Phe Leu
2065                2070                2075                2080
Trp Asn Cys Ala Leu Ser Val Val Lys Glu Gly Arg Ser Val Val Leu
                2085                2090                2095
Thr Ser His Ser Met Glu Glu Cys Glu Ala Leu Cys Thr Arg Met Ala
            2100                2105                2110
Ile Met Val Asn Gly Arg Phe Arg Cys Leu Gly Ser Val Gln His Leu
        2115                2120                2125
Lys Asn Arg Phe Gly Asp Gly Tyr Thr Ile Val Val Arg Ile Ala Gly
    2130                2135                2140
Ser Asn Pro Asp Leu Lys Pro Val Gln Asp Phe Phe Gly Leu Ala Phe
2145                2150                2155                2160
Pro Gly Ser Val Leu Lys Glu Lys His Arg Asn Met Leu Gln Tyr Gln
                2165                2170                2175
Leu Pro Ser Ser Leu Ser Ser Leu Ala Arg Ile Phe Ser Ile Leu Ser
            2180                2185                2190
Gln Ser Lys Lys Arg Leu His Ile Glu Asp Tyr Ser Val Ser Gln Thr
        2195                2200                2205
Thr Leu Asp Gln Val Phe Val Asn Phe Ala Lys Asp Gln Ser Asp Asp
    2210                2215                2220
Asp His Leu Lys Asp Leu Ser Leu His Lys Asn Gln Thr Val Val Asp
2225                2230                2235                2240
Val Ala Val Leu Thr Ser Phe Leu Gln Asp Glu Lys Val Lys Glu Ser
                2245                2250                2255
Tyr Val
```

<210> SEQ ID NO 3
<211> LENGTH: 18
<212> TYPE: PRT
<213> ORGANISM: Homo sapiens

<400> SEQUENCE: 3

```
Lys Glu Ala Arg Leu Lys Glu Thr Met Arg Ile Met Gly Leu Asp Asn
  1               5                  10                  15
Ser Ile
```

<210> SEQ ID NO 4
<211> LENGTH: 5
<212> TYPE: PRT
<213> ORGANISM: Homo sapiens

<400> SEQUENCE: 4

Phe Ser Arg Ala Asn

```
<210> SEQ ID NO 5
<211> LENGTH: 26
<212> TYPE: PRT
<213> ORGANISM: Homo sapiens

<400> SEQUENCE: 5

Ala Leu Phe Glu Glu Gln Gly Ile Gly Val Gln Trp Asp Asn Leu Phe
 1               5                  10                  15

Glu Ser Pro Val Glu Glu Asp Gly Phe Asn
             20                  25

<210> SEQ ID NO 6
<211> LENGTH: 284
<212> TYPE: PRT
<213> ORGANISM: Homo sapiens

<400> SEQUENCE: 6

Phe Gly Lys Tyr Pro Ser Leu Glu Leu Gln Pro Trp Met Tyr Asn Glu
 1               5                  10                  15

Gln Tyr Thr Phe Val Ser Asn Asp Ala Pro Glu Asp Thr Gly Thr Leu
             20                  25                  30

Glu Leu Leu Asn Ala Leu Thr Lys Asp Pro Gly Phe Gly Thr Arg Cys
         35                  40                  45

Met Glu Gly Asn Pro Ile Pro Asp Thr Pro Cys Gln Ala Gly Glu Glu
     50                  55                  60

Glu Trp Thr Thr Ala Pro Val Pro Gln Thr Ile Met Asp Leu Phe Gln
 65                  70                  75                  80

Asn Gly Asn Trp Thr Met Gln Asn Pro Ser Pro Ala Cys Gln Cys Ser
                 85                  90                  95

Ser Asp Lys Ile Lys Lys Met Leu Pro Val Cys Pro Pro Gly Ala Gly
            100                 105                 110

Gly Leu Pro Pro Pro Gln Arg Lys Gln Asn Thr Ala Asp Ile Leu Gln
        115                 120                 125

Asp Leu Thr Gly Arg Asn Ile Ser Asp Tyr Leu Val Lys Thr Tyr Val
130                 135                 140

Gln Ile Ile Ala Lys Ser Leu Lys Asn Lys Ile Trp Val Asn Glu Phe
145                 150                 155                 160

Arg Tyr Gly Gly Phe Ser Leu Gly Val Ser Asn Thr Gln Ala Leu Pro
                165                 170                 175

Pro Ser Gln Glu Val Asn Asp Ala Ile Lys Gln Met Lys Lys His Leu
            180                 185                 190

Lys Leu Ala Lys Asp Ser Ser Ala Asp Arg Phe Leu Asn Ser Leu Gly
        195                 200                 205

Arg Phe Met Thr Gly Leu Asp Thr Arg Asn Asn Val Lys Val Trp Phe
    210                 215                 220

Asn Asn Lys Gly Trp His Ala Ile Ser Ser Phe Leu Asn Val Ile Asn
225                 230                 235                 240

Asn Ala Ile Leu Arg Ala Asn Leu Gln Lys Gly Glu Asn Pro Ser His
                245                 250                 255

Tyr Gly Ile Thr Ala Phe Asn His Pro Leu Asn Leu Thr Lys Gln Gln
            260                 265                 270

Leu Ser Glu Val Ala Leu Met Thr Thr Ser Val Asp
        275                 280
```

```
<210> SEQ ID NO 7
<211> LENGTH: 23
<212> TYPE: PRT
<213> ORGANISM: Homo sapiens

<400> SEQUENCE: 7

Leu Leu Leu Leu Tyr Gly Trp Ser Ile Thr Pro Leu Met Tyr Pro Ala
 1               5                  10                  15

Ser Phe Val Phe Lys Ile Pro
            20

<210> SEQ ID NO 8
<211> LENGTH: 29
<212> TYPE: PRT
<213> ORGANISM: Homo sapiens

<400> SEQUENCE: 8

Val Lys Asn Gln Ala Met Ala Asp Ala Leu Glu Arg Phe Gly Glu Asn
 1               5                  10                  15

Arg Phe Val Ser Pro Leu Ser Trp Asp Leu Val Gly Arg
            20                  25

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 9
gtcacttccc aaacaaagct a                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 10
atggacgcat tgaagtttcc                                              20

<210> SEQ ID NO 11
<211> LENGTH: 15
<212> TYPE: DNA
<213> ORGANISM: chicken

<400> SEQUENCE: 11
accaggggaa tctcc                                                   15

<210> SEQ ID NO 12
<211> LENGTH: 15
<212> TYPE: DNA
<213> ORGANISM: chicken

<400> SEQUENCE: 12
accagggaaa tctcc                                                   15

<210> SEQ ID NO 13
<211> LENGTH: 15
<212> TYPE: PRT
<213> ORGANISM: Homo sapiens

<400> SEQUENCE: 13
```

-continued

```
Arg Tyr Pro Thr Pro Gly Glu Ala Pro Gly Val Val Gly Asn Phe
 1               5                  10                  15

<210> SEQ ID NO 14
<211> LENGTH: 15
<212> TYPE: PRT
<213> ORGANISM: mouse

<400> SEQUENCE: 14

Arg Tyr Pro Thr Pro Gly Glu Ala Pro Gly Val Val Gly Asn Phe
 1               5                  10                  15

<210> SEQ ID NO 15
<211> LENGTH: 15
<212> TYPE: PRT
<213> ORGANISM: Takifugu Rubripes

<400> SEQUENCE: 15

Ser His Pro Thr Leu Gly Glu Thr Pro Gly Gln Val Asn Asn Phe
 1               5                  10                  15

<210> SEQ ID NO 16
<211> LENGTH: 15
<212> TYPE: PRT
<213> ORGANISM: chicken

<400> SEQUENCE: 16

Arg Tyr Pro Thr Pro Gly Glu Ser Pro Gly Ile Val Gly Asn Phe
 1               5                  10                  15

<210> SEQ ID NO 17
<211> LENGTH: 15
<212> TYPE: PRT
<213> ORGANISM: chicken

<400> SEQUENCE: 17

Arg Tyr Pro Thr Pro Gly Lys Ser Pro Gly Ile Val Gly Asn Phe
 1               5                  10                  15

<210> SEQ ID NO 18
<211> LENGTH: 45
<212> TYPE: DNA
<213> ORGANISM: chicken

<400> SEQUENCE: 18
cgctacccaa caccagggga atctcctggt attgttggaa acttc            45

<210> SEQ ID NO 19
<211> LENGTH: 45
<212> TYPE: DNA
<213> ORGANISM: chicken

<400> SEQUENCE: 19
cgctacccaa caccagggaa atctcctggt attgttggaa acttc            45
```